(12) United States Patent
Phillips

(10) Patent No.: US 11,361,386 B2
(45) Date of Patent: Jun. 14, 2022

(54) SYSTEMS AND METHODS FOR AUTOMATED REPATRIATION OF A PATIENT FROM AN OUT-OF-NETWORK ADMITTING HOSPITAL TO AN IN-NETWORK DESTINATION HOSPITAL

(71) Applicant: Rachel Phillips, San Pedro, CA (US)

(72) Inventor: Rachel Phillips, San Pedro, CA (US)

( * ) Notice: Subject to any disclaimer, the term of this patent is extended or adjusted under 35 U.S.C. 154(b) by 53 days.

(21) Appl. No.: 16/751,560

(22) Filed: Jan. 24, 2020

(65) Prior Publication Data
US 2020/0160950 A1    May 21, 2020

Related U.S. Application Data

(63) Continuation of application No. 15/815,560, filed on Nov. 16, 2017, now abandoned, which is a
(Continued)

(51) Int. Cl.
   *G06Q 40/08* (2012.01)
   *G06Q 10/10* (2012.01)
   (Continued)

(52) U.S. Cl.
   CPC ....... *G06Q 40/08* (2013.01); *G06Q 10/06311* (2013.01); *G06Q 10/10* (2013.01);
   (Continued)

(58) Field of Classification Search
   CPC ........ G16H 10/60; G16H 40/20; G16H 80/00; G06Q 10/10; G06Q 50/22; G06Q 10/06;
   (Continued)

(56) References Cited

U.S. PATENT DOCUMENTS

| 5,301,105 A | 4/1994 | Cummings, Jr. |
| 5,748,907 A | 5/1998 | Crane |

(Continued)

FOREIGN PATENT DOCUMENTS

| JP | 2011 070668 A | 4/2011 |
| WO | WO 2013/033655 A1 | 3/2013 |

OTHER PUBLICATIONS

Out-Of-Network Ambulance Rides Can Bring Out-Of-Pocket Expenses, Michelle Andrews, www.khn.org, Jun. 14, 2011 (Year: 2011).*
(Continued)

*Primary Examiner* — Joseph D Burgess
(74) *Attorney, Agent, or Firm* — Knobbe, Martens, Olson & Bear, LLP

(57) ABSTRACT

A system server stores and allows access to patient data, and can include a repatriation management system and/or a discharge management system. The repatriation management system provides for transfer of a patient from an admitting out-of-network hospital to a destination in-network hospital. The repatriation management system includes a computer program for analyzing the patient data, analyzing candidate destination hospital data, and calculating matches between the two. The discharge management system provides for transfer of a patient from an acute care hospital environment to a remote care facility. The discharge management system includes a computer program for analyzing the patient data, identifying and formulating resolutions to placement problems, and determining if the patient will be discharged. The system server is networked to allow remote access to the stored data and communication between the admitting hospital, destination hospitals, remote care facilities, and medical transport providers.

17 Claims, 26 Drawing Sheets

Related U.S. Application Data continuation of application No. 14/660,287, filed on Mar. 17, 2015, now abandoned, which is a continuation of application No. 14/081,362, filed on Nov. 15, 2013, now abandoned.

(60) Provisional application No. 61/726,745, filed on Nov. 15, 2012.

(51) Int. Cl.
| | |
|---|---|
| *G16H 40/20* | (2018.01) |
| *G16H 40/67* | (2018.01) |
| *G06Q 10/06* | (2012.01) |
| *G16H 10/60* | (2018.01) |

(52) U.S. Cl.
CPC ............ *G16H 10/60* (2018.01); *G16H 40/20* (2018.01); *G16H 40/67* (2018.01)

(58) Field of Classification Search
CPC ........ G06Q 10/00; G06Q 10/08; G06Q 40/08; A61G 3/001; A61G 2210/30
See application file for complete search history.

(56) References Cited

U.S. PATENT DOCUMENTS

| | | | |
|---|---|---|---|
| 5,903,889 A | 5/1999 | de la Huerga et al. | |
| 6,389,454 B1 | 5/2002 | Ralston et al. | |
| 7,578,432 B2 | 8/2009 | Libin et al. | |
| 7,711,579 B2 | 5/2010 | Lancaster et al. | |
| 7,756,723 B2 | 7/2010 | Rosow et al. | |
| 8,010,386 B2 * | 8/2011 | Wyatt .................... | G06Q 10/10 |
| | | | 705/4 |
| 8,065,167 B1 | 11/2011 | Wyman | |
| 8,428,961 B2 | 4/2013 | Greischar et al. | |
| 2002/0072911 A1 | 6/2002 | Kilgore et al. | |
| 2003/0197062 A1 * | 10/2003 | Shaw ................... | G06K 17/0022 |
| | | | 235/385 |
| 2004/0128168 A1 * | 7/2004 | Wyatt .................... | G06Q 10/02 |
| | | | 707/999.009 |
| 2007/0156455 A1 * | 7/2007 | Tarino .................... | G06Q 10/00 |
| | | | 705/2 |
| 2007/0214011 A1 | 9/2007 | Demers | |
| 2009/0222539 A1 * | 9/2009 | Lewis .................... | G16H 10/60 |
| | | | 709/221 |
| 2013/0046551 A1 | 2/2013 | Vahle et al. | |
| 2013/0054271 A1 | 2/2013 | Langford et al. | |
| 2013/0096942 A1 | 4/2013 | Bowles et al. | |
| 2013/0268284 A1 * | 10/2013 | Heck .................... | G06Q 10/107 |
| | | | 705/2 |
| 2014/0136223 A1 | 5/2014 | Phillips | |
| 2015/0254405 A1 | 9/2015 | Phillips | |
| 2018/0166158 A1 | 6/2018 | Phillips | |

OTHER PUBLICATIONS

S. T. Konstantinidis, P. D. Bamidis, S. Marolov and C. Pappas, "The TraPa System: A Web-Based System to Improve Cross-Border Patient Transfers," Twentieth IEEE International Symposium on Computer-Based Medical Systems (CBMS'07), 2007, pp. 325-330 (Year: 2007).*

* cited by examiner

SYSTEMS AND METHODS FOR AUTOMATED REPATRIATION OF A PATIENT FROM AN OUT-OF-NETWORK ADMITTING HOSPITAL TO AN IN-NETWORK DESTINATION HOSPITAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 and made a part of this specification.

BACKGROUND

Field

This disclosure relates generally to a hospital patient case management system, including for example systems and methods for automated repatriation of a patient from an out-of-network hospitals to an in-network hospitals; and/or systems and methods for automated patient discharge management.

Background

Patients are often admitted to hospitals which are not covered, or not fully covered by the patients' insurer. This can be particularly true in the case of emergencies, in which case the patient is often taken to the most convenient hospital, irrespective of the patient's insurance status. However, costs accrued by the patient during her stay in an out-of-network hospital risk going unpaid if the patient's insurer does not cover them, and the patient herself is unwilling or unable to make payment. Accordingly, once such a patient is sufficiently medically stable, it is often desirable to transfer the patient from the out-of-network hospital to which she has been admitted, to an appropriate in-network hospital. This process is referred to herein as "repatriation". In order to repatriate patients from out-of-network to in-network hospitals or other medical facilities, a great deal of planning often takes place, involving numerous back-and-forth communications between a case worker at the admitting hospital, staff at the destination hospital, and medical transport providers, often involving a number of telephone calls and fax communications of voluminous patient data.

Acute care patients who are hospitalized with a medical condition and are not medically stable typically become sufficiently medically stable to be discharged from the acute care hospital setting but may have a chronic condition and continue to require skilled nursing care. These patients typically are transferred to medical facilities that rank below an acute care hospital but include a skilled nursing staff and/or physicians on-call to tend to the patient's medical needs. Managing this discharge of patients typically involves numerous back-and-forth communications between multiple facilities and case managers, hospital visits, patient evaluations, and reviewing of evaluation reports by both the hospital case manager and the case managers of a plurality of sub-acute facilities, resulting in a very time consuming and costly process.

SUMMARY

In some embodiments, a non-transitory computer storage medium has stored thereon a computer program for repatriating a patient from an out-of-network admitting hospital to an in-network destination hospital, said program comprising: first instructions that, when executed by computer hardware, automatically match the patient to one or more candidate destination hospitals, wherein the first instructions cause the computer hardware to: access from a computer storage medium patient data, the data including at least insurance network information for the patient; access from a computer storage medium data regarding candidate destination hospitals, the data including at least insurance network information for the candidate destination hospitals; and automatically match the patient to one or more of the candidate destination hospitals based at least upon matching the insurance network information of the patient and the insurance network information of the candidate destination hospitals. The program further comprises second instructions that, when executed by computer hardware, handles selection and repatriation requests for candidate destination hospitals and repatriates the patient from the out-of-network admitting hospital to the in-network destination hospital, wherein the second instructions cause the computer hardware to: automatically generate a list of candidate destination hospitals automatically matched to the patient; electronically transmit, to the admitting hospital, the list of candidate destination hospitals matched to the patient; electronically receive a repatriation request from the admitting hospital, the repatriation request indicating a selected destination hospital from among the list of the one or more candidate destination hospitals matched to the patient, and electronically transmit the request to the selected destination hospital; and electronically receive an acceptance of the repatriation request from the selected destination hospital and electronically transmit the acceptance to the admitting hospital. The program further comprises third instructions that, when executed by computer hardware, electronically arrange patient transport, wherein the third instructions cause the computer hardware to: electronically receive, from the admitting hospital, an ambulance request to schedule transport of the patient to the selected destination hospital, and electronically transmit the ambulance request to the one or more ambulance providers; and electronically receive, from one of the ambulance providers, acceptance of the ambulance request, and electronically transmit acceptance of the ambulance request to the admitting hospital.

In some embodiments, the program further comprises fourth instructions that, when executed by computer hardware, cause the computer hardware to receive a patient-specific code, and in response to receiving the patient-specific code, automatically access the patient data. In some embodiments, the patient-specific code is received from a QR scanner or barcode scanner. In some embodiments, the patient-specific code indicates admission to the admitting hospital, and the fourth instructions cause the hardware to automatically alert an insurer of the patient upon receiving the patient-specific code indicating admission to the admitting hospital. In some embodiments, the patient data further includes one or more medical parameters of the patient, the data regarding candidate destination hospitals includes one or more clinical capabilities of the candidate destination hospitals, and the automatically matching the patient to one or more of the candidate destination hospitals is further based at least upon matching the medical parameters of the patient and the clinical capabilities of the candidate destination hospitals. In some embodiments, the insurance network information of the patient includes a list of ambulance providers associated with an insurer of the patient, and the third instructions cause the computer hardware to electronically transmit the ambulance request only to ambulance providers from the list of associated ambulance providers. In some embodiments, the third instructions further cause the computer hardware to: electronically receive, from three or more of the ambulance providers, acceptance of the ambulance request, and electronically transmit the acceptances of the ambulance request to the admitting hospital, and electronically receive, from the admitting hospital, a selection from among the accepting ambulance providers. In some embodiments, the third instructions further cause the computer hardware to electronically notify an insurer of the patient of the selected ambulance provider.

According to another embodiment, a method for repatriating a patient from an out-of-network admitting hospital to an in-network destination hospital comprises: automatically matching the patient to one or more candidate destination hospitals, wherein the automatically matching comprises: accessing from a computer storage medium patient data including at least insurance network information for the patient; accessing from a computer storage medium data regarding candidate destination hospitals, the data including at least insurance network information for the candidate destination hospitals; and automatically matching, using computer hardware, the patient to one or more of the candidate destination hospitals based at least upon matching the insurance network information of the patient and the insurance network information of the candidate destination hospitals. The method further comprises handling, using computer hardware, a request to repatriate the patient from the out-of-network admitting hospital to the in-network destination hospital, wherein the handling comprises: electronically transmitting, to the admitting hospital, a list of the one or more candidate destination hospitals matched to the patient; electronically receiving a repatriation request from the admitting hospital, the repatriation request indicating a selected destination hospital from among the list of the one or more candidate destination hospitals matched to the patient, and electronically transmitting the request to the selected destination hospital; and electronically receiving an acceptance of the repatriation request from the selected destination hospital and electronically transmitting the acceptance to the admitting hospital. The method further comprises electronically arranging, using computer hardware, patient transport, the electronically arranging comprising: electronically receiving, from the admitting hospital, an ambulance request to schedule transport of the patient to the selected destination hospital, and electronically transmitting the ambulance request to the one or more ambulance providers; and electronically receiving, from at least one of the ambulance providers, acceptance of the ambulance request, and electronically transmitting acceptance of the ambulance request to the admitting hospital.

In some embodiments, the method further comprises receiving a patient-specific code from a QR or barcode scanner, and in response to receiving the patient-specific code, automatically accessing the patient data. In some embodiments, the patient-specific code indicates admission to the admitting hospital, the method further comprising automatically alerting an insurer of the patient upon receiving the patient-specific code indicating admission to the admitting hospital. In some embodiments, the patient data further includes one or more medical parameters of the patient, the data regarding candidate destination hospitals includes one or more clinical capabilities of the candidate destination hospitals, and the automatically matching the patient to one or more of the candidate destination hospitals is further based at least upon matching the medical parameters of the patient and the clinical capabilities of the candidate destination hospitals. In some embodiments, the insurance network information of the patient includes a list of ambulance providers associated with the patient's insurer, the method further comprising transmitting the ambulance request only to ambulance providers from the list of associated ambulance providers. In some embodiments, the method further comprises electronically receiving, from three or more of the ambulance providers, acceptance of the ambulance request, and electronically transmitting the acceptances of the ambulance request to the admitting hospital; electronically receiving, from the admitting hospital, a selection from among the accepting ambulance providers; and electronically notifying an insurer of the patient of the selected ambulance provider.

In accordance with another embodiment, a system for repatriating a patient from an out-of-network admitting hospital to an in-network destination hospital, comprises: one or more computing devices; and physical computer storage that stores data comprising: patient data including at least insurance network information for the patient; candidate destination hospital data including at least insurance network information for candidate destination hospitals. The system further comprises an admitting hospital module comprising instructions stored on one or more computer memory devices that, when executed by one or more hardware processors, cause the admitting hospital module to: provide an interface to receive a request to match a patient admitted to the admitting hospital to one or more candidate destination hospitals, said matching based at least upon matching the insurance network information of the patient and the insurance network information of the candidate destination hospitals; automatically match one or more candidate destination hospitals to the patient; list the one or more candidate destination hospitals matched to the patient; receive a repatriation request indicating a selected destination hospital from among the listed one or more candidate destination hospitals matched to the patient; indicate that the selected destination hospital has accepted the repatriation request; electronically arrange transport of the patient to the selected destination hospital; and indicate acceptance of the transport request from one or more medical transport providers. The system further comprises a destination hospital module comprising instructions stored on one or more computer memory devices that, when executed by one or more hardware processors, cause the destination hospital module to: indicate the receipt of a repatriation request from the admitting hospital; and receive an acceptance of the repatriation request from the destination hospital. The system further comprises a medical transport provider module comprising instructions stored on one or more computer memory devices that, when executed by one or more hardware processors, cause the medical transport provider module to: indicate the transport request from the admitting hospital; and receive an acceptance of the transport request from the medical transport provider.

In some embodiments, the admitting hospital module further comprises instructions stored on one or more computer memory devices that, when executed by one or more hardware processors, cause the admitting hospital module to display an indication that a patient-specific code may be entered by scanning a QR code or barcode to automatically obtain patient data. In some embodiments, the insurance network information of the patient includes a list of medical transport providers associated with the patient's insurer, and the medical transport provider module only displays an indication of the transport request from the admitting hospital for medical transport providers from the list of medical transport providers associated with the patient's insurer. In some embodiments, the admitting hospital module further comprises instructions stored on one or more computer memory devices that, when executed by one or more hardware processors, cause the admitting hospital module to: indicate acceptances of the transport request from three or more of the medical transport providers; and receives a selection of one of the accepting medical transport providers. In some embodiments, the admitting hospital module further comprises instructions stored on one or more computer memory devices that, when executed by one or more hardware processors, cause the admitting hospital module to receive a request to alert an insurer of the patient of the selection of the accepting medical transport provider. In some embodiments, the medical transport provider module further comprises instructions stored on one or more memory devices that, when executed by one or more hardware processors, cause the medical transport module to indicate that the transport request from the admitting hospital has been cancelled.

Additional embodiments disclosed herein provide an case management system and method for placement of a patient from an acute care hospital environment to a remote care facility for convalescing care. The function is to employ a secure online interactive computerized system for planning, arranging and executing the placement of a patient who no longer requires hospitalization but still requires some level of health care assistance, typically at a remote health care facility.

The clinical data and medical parameters of the patient can be monitored and entered into a portable data entry terminal on a daily basis by the bedside nurse during shift reports. This system does not require the intervention of a designated hospital case manager. The entered clinical data can then be wirelessly transferred to an off-site remotely located system server for storage and future access. A computer program associated with the system server may analyze the entered data and the condition of the patient. As a result of the analysis of the entered data, abnormal readings can be noted thus identifying patient medical and hospital placement discharge issues. These patient medical and hospital discharge issues can be flagged so that the medical staff is alerted to these conditions. Finally, resolutions to these issues can be formulated for implementation by the hospital medical staff so that the patient can be discharged. The clinical data can be entered and stored within a system data storage memory and subsequently retrieved upon request. An electronic communications network can be in electronic communication with the system server and a plurality of remote health care facilities for enabling access to the data stored in the system data storage memory. The entered and stored data can be accessible from both the portable data entry terminals and the remote care facilities once the patient case has been offered to a remote care facility. Furthermore, cyber communications between the remote care facilities and the portable data entry terminals over the network can facilitate the placement of the patient in one of the remote care facilities upon discharge of the patient from the acute-care hospital environment.

In one embodiment, the plurality of portable data entry terminals can include notebook computers, smartphones, or personal digital assistants (PDA's). These devices are easily portable and enable the nursing professional to carry the data entry terminal from patient-to-patient during her morning visits for entering monitored clinical parameters such as body temperature, blood pressure and pulse readings. The data manually entered into the notebook computer is conveniently wirelessly transferred to the off-site system server. However, the data could be downloaded into a local desktop computer via a cable port connection or via a cradle associated with the desktop computer and designed to transfer the recorded data. The data stored in the system data storage memory can be securely accessed via a password by employing the network in an interactive mode for enabling cyber communications between the components of the case management system. Typical components such as a printer, scanner and photocopier can be associated with the case management system. The system can be programmed to provide continuous matching of hospital patients to real-time open discharge facility beds based at least in part on details of acceptable isolation combinations, gender, insurance payer, etc., which are entered in by the discharge facility intake staff, as the discharge facility beds become available. The system thereby increases the opportunity for capturing beds in a more timely manner. Matched case information and a summarized clinical evaluation can be sent to the discharge facility providing the facility with the ability to more quickly view the status and needs of the patient. The system may be configured to alert the hospital case manager if entered clinical information is not compatible with the level of discharge facility ordered by a physician. The system may further create a specific list of all inappropriate clinical states for the hospital case manager and physician, along with providing problem-solving algorithms for these inappropriate clinical states so that a more appropriate level of discharge facility may be ordered and/or the identified clinical issues may be resolved. In this way, the original physician order for the level of care may be satisfied, thus avoiding unsafe transfers of patients to discharge facilities which do not provide the appropriate level of medical care. In a series of proprietary electronic interactions between multiple hospitals and case managers, the discharge facilities are able to confirm the acceptance of the chosen patient without the need for phone calls or further faxes. The system can alert non-chosen patient case managers that the bed has been reserved or closed for submissions so that the case manager may then proceed to submit to other available beds on the system. The system allows for the hospital case manager to electronically withdraw the acceptance of the bed if the patient's condition deteriorates before transfer, and also allows for the hospital case manager to request a short-term hold which holds the facility bed for a designated period of time. The discharge facility may have the capability to tag patients on the system that require a return from their facility to an acute hospital for temporary higher level medical care, thereby assuring that the patient returns to their facility during the subsequent discharge process. The system may alert the discharge facility when a submission of their tagged patient has been entered by the hospital case manager, thereby allowing the discharge facility to facilitate an open bed if possible. The discharge facility may have the capability of assigning a hold on the bed for the patient who requires a return to the hospital for higher level care, thereby alerting hospital nurses and/or case managers that a bed is on hold and the duration of the hold.

The system may also allow for the discharge facility to submit desired times of patient arrival for admission to the discharge facility to the hospital nurse or case manager. The system can additionally allow for online requests for ambulance transfers by the hospital case manager or nurse to multiple ambulance companies with the information such as desired arrival time to the designated discharge facility, level of transport required, specific clinical information, etc. In addition, contracted ambulance companies may be highlighted to ensure the cost-effective use of hospital-contracted services. Multiple ambulance companies may then respond by electronic submission regarding the times that they would be available to transport the patient. The hospital case manager or nurse can then select an ambulance provider, confirm the company and the transport electronically without the need for phone calls or faxes. The system may also allow the ambulance company to electronically notify the hospital case manager, nurse, patient, family member, and/or physician of a delay in transport and/or a cancellation of transport. The hospital case manager or nurse may have the capability to withdraw or cancel the ambulance transport via an online interface.

In some embodiments, the system may provide the patient and family with an access code to designated sites on the system which provide resources to assist in selecting a discharge facility. For example, such sites may provide video education modules regarding discharge facility levels of care and services, the ability to search for multiple facilities, view discharge facility marketing materials and "virtual visit" videos. Patients and families may additionally rate discharge facility preferences with a numeric rating system which may then electronically alert the hospital case manager or nurse of the designated preferences. The system may provide the name and contact information of the designated hospital case manager to the patient and family, and can update this information as the designated case manager assignments change during the hospital stay. The system may provide the patient and/or family the ability to request a meeting from the case manager online. The system also may provide the patient and/or family of the changing status of the discharge and ultimately the name of the accepting discharge facility, the assigned physician's contact information and the scheduled time of the ambulance transfer to the facility.

The system can also allow for the viewing of discharge clinical information to be viewed off-site by physicians, allowing the physicians to accept or decline referrals of discharge facility patients. The system can also provide the name and contact information of the hospital case manager as assignments change and informs the physicians of the status of the discharge, the accepting discharge facility, and time of arrival once a successful placement has been completed.

An additional feature includes a computer program that automatically instructs the system server to transmit a signal across the network to a mobile communications device for indicating when a threshold condition has occurred and corresponding data has been entered into the system data storage memory for clinically sensitive cases. The signal transmitted by the system server can include audio beeps or text messaging and be specialty-specific, directed to one or more physicians practicing in a relevant medical specialty. Furthermore, the subject matter of the text message can be listed on the physician's "general menu" or "personalized menu" relating to a certain medical case. An example of the mobile communications device is a smart phone, cell phone, PDA, or other suitable apparatus carried by physician(s) who respond to the transmitted signal. Another feature enables the computer program to automatically instruct the system server to recognize a secure password transmitted to the system server over the network from one of the remote care facilities for obtaining access to the data stored in the system data storage memory for investigating the condition of the patient.

A further feature enables the payer and/or provider of the medical care such as, for example, an insurance company or Independent Physician Association to have daily access to patient clinical information and case management forms. In addition, the system server can compare the data entered into the portable data entry terminals and stored in the system data storage memory with a criteria profile of one of the remote facilities, that is, an insurance company. The criteria profile sets forth the requirements to determine if the patient is an insured of the insurance company and what the limitations of the insured's policy are and whether an enforceable policy exists. In this manner, the criteria profile programmed into the computer program will automatically authorize or deny the patient expenses, or refer the decision to a medical review panel within the insurance company and/or Independent Physician Association. This design eliminates the requirement of ongoing telephone conferences between the case managers of the hospital and the case managers of the insurance company regarding expense authorization approvals and denials. Another feature is directed to electronic billing for services rendered. After the patient treatment program has terminated, the financial records associated with the treatment program can enable the generation of a billing statement to be transmitted from the hospital to the appropriate managed care provider or insurance company for reimbursement of expenses and charges associated with treating the patient. The billing statements can be transmitted in electronic format or as a paper document. Likewise, billing statements can be generated for presentation to other medical insurance plans such as, for example, the California State Medi-Cal program or the Federal Medicare program. All of the information required to generate a billing statement for either the state or federal medical programs may be included in the original entered data collected daily by the staff nursing personnel.

In one embodiment, the interactive/integrated case management system and method for use in an acute care hospital environment for placement of a patient upon discharge from the acute care hospital environment to a remote care facility including a plurality of portable data entry terminals for entering data for monitoring medical parameters of a patient in a hospital environment. A remotely located system server is wirelessly connected to the portable data entry terminals for receiving, storing and providing access to the entered data, the system server including a computer program for analyzing the entered data, identifying and formulating resolutions to patient and discharge placement problems, and determining if and at what level the patient will be discharged. A system data storage memory is housed within the system server for depositing and retrieving the entered data. A network is in cyber communication with the system server and a plurality of remote care facilities in a secure online interactive mode for enabling access to the data stored in the system data storage memory from the portable data entry terminals and the remote care facilities, Likewise, the network enables cyber communications between the remote care facilities and the portable data entry terminals in a secure online interactive mode for placement of the patient in one of the remote care facilities upon discharge of the patient from the hospital environment.

BRIEF DESCRIPTION OF THE DRAWINGS

Some embodiments are depicted in the accompanying drawings for illustrative purposes, and should in no way be interpreted as limiting the scope of the inventions described herein. In addition, various features of different disclosed embodiments can be combined to form additional embodiments, which are part of this disclosure. Any feature or structure can be removed or omitted. Throughout the drawings, reference numbers may be reused to indicate correspondence between reference elements.

FIG. 4B illustrates an example user interface.

FIGS. 5B-5D illustrate example user interfaces.

FIGS. 6B-6E illustrates example user interfaces.

DETAILED DESCRIPTION

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Case Management System Overview

Figure 1:
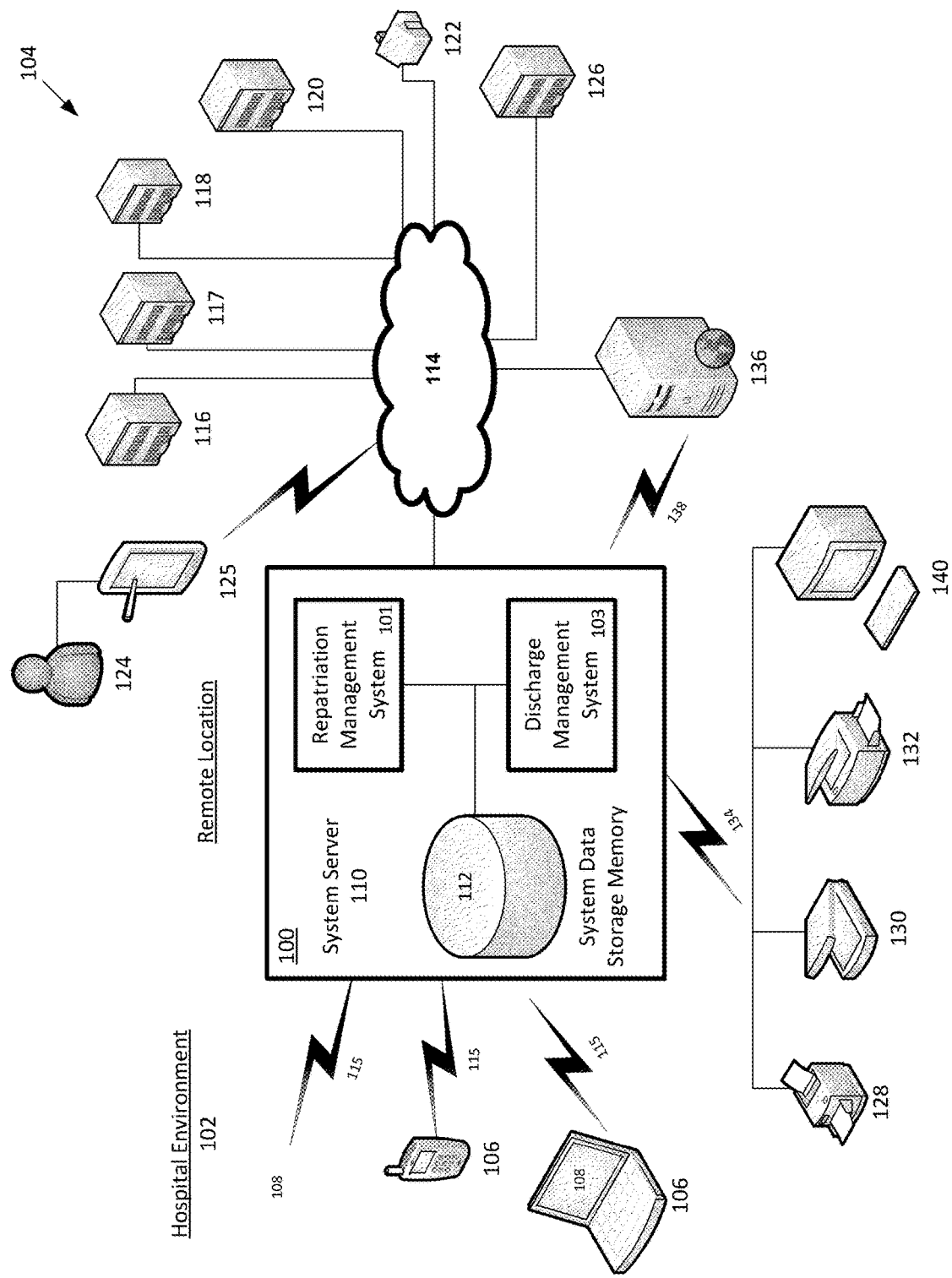
FIG. 1 illustrates an example system and operating environment.

FIG. 1 illustrates an example system and operating environment. The case management system 100 may include one or more servers or other computer systems. The system 100 may include a system server 110, system data storage memory 112, a repatriation management system 101, and a discharge management system 103. In some embodiments, the system 100 may include the repatriation management system 101, but not the discharge management system 103, or vice versa.

One function of the system 100 is the placement of a patient (not shown) from the admitting acute care hospital environment to one of a plurality of remote care facilities 104 upon discharge of the patient from the acute care hospital environment for convalescing sub-acute, or for repatriation to an in-network destination hospital. This can accomplished by employing a secure online interactive computerized system for planning, arranging and executing repatriation or discharge processes for a patient who no longer requires hospitalization but still requires some level of health care assistance. The health care assistance is typically provided at a remote health care facility 104.

The system 100 is described below and schematically disclosed in FIG. 1. One of a plurality of portable data entry terminals 106 can be in wireless (or wired) communication with the system 100. The portable data entry terminals 106 can include, for example, a QR or barcode scanner to scan a code associated with a patient upon admission. Additionally or alternatively, portable data entry terminals 106 may enable a staff nurse to enter the clinical data and medical parameters of the patient such as, for example, body temperature, blood pressure and respiratory rate. The portability feature enables the staff nurse to transport the data entry terminal 106 from one patient to the next patient during the morning rounds as the nurse visits each patient. Any suitable data entry terminal 106 that is portable and useful in serving as an input data entry point can be employed.

In a remote location off-site of the hospital environment is a system server 110 which serves several functions. In general, the system server 110 can perform all the functions of a hospital case manager including (1) providing a storage site for patient data entered in the portable data entry terminals 106 via a system data storage memory 112 located within the system server 110, (2) providing an analytical function by employing a computer program for analyzing the entered data via the repatriation management system 101 and/or the discharge management system 103, and identifying, informing of the existence of, and formulating resolutions for patient medical and discharge related problems, and (3) functioning as a conduit for the transmission of messages between the portable data entry terminals 106 and any of the remote care facilities 104 via a network 114 as shown in FIG. 1. The capacity of medical data accumulated in the system server 110 enhances the patient course, that is, it improves the quality of health care afforded the patient because the case management system 100 includes (a) comprehensive clinical information such as respiratory, gastrointestinal, neurological, vital sign and medical data, (b) laboratory test results such as complete blood count and chemistry, and (c) culture test results including blood/urine, sputum and stool of the patient.

The clinical data entered into the portable data entry terminals 106 can be wirelessly transmitted as is known in the art and illustrated by a wireless link 115 to the off-site, remotely located system server 110 for storage and future access. Consequently, the portable data entry terminals 106 provide multiple entry points but all of the data can be transmitted wirelessly as illustrated by the wireless link 115 and stored on the system server 110. The entered clinical data which is utilized to generate the patient medical reports can be stored in the system data storage memory 112 as shown in FIG. 1 and subsequently retrieved upon request. Instead of wirelessly transmitting the entered clinical data to the system server 110, the data manually entered into the portable data entry terminals 106 could alternately be downloaded into a local desktop computer via a cable port connection or via a contact cradle arrangement associated with the desktop computer to transfer the recorded data. The data entered and stored in the system data storage memory 112 can be securely accessed via a password by employing the network 114 in an interactive mode for enabling cyber communications between the components of the case management system 100. Typically peripheral components such as a printer 128, a scanner 130 and a photocopier 132 can be wirelessly associated with the case management system 100 at the remote location or within the hospital environment as shown by a wireless link 134 in FIG. 1. Of course, the printer 128, scanner 130 and photocopier 132 can be incorporated into a single multifunction apparatus (not shown), if desired.

Other information can also be entered into the system data storage memory 112 in order to ensure that the case management system 100 is useful and functional. Communications with the acute care hospital 102 and the remote care facilities 104 may be maintained on a daily basis to collect data and information regarding the status of bed availability including the type of bed availability as it relates to the type of infirmity the bed is dedicated to, type of patient accommodated in the respective remote care facility 104, number of beds available, the range of medical problems that a particular remote care facility 104 can accommodate, and the like. The collection of this type of data and the evaluation thereof will occur on a daily basis and this information will be stored and constantly updated in the system data storage memory 112. This information may be accessible to password authorized personnel via computer located in the acute care hospital 102 (i.e., portable data entry terminals 106 and other hospital computers 140 shown in FIG. 1), the remote care facilities 104, and managed care providers or insurance companies 126. The case management system 100 can be utilized for patient management within the acute care hospital 102 and outpatient management of patients located in cooperating remote care facilities 104.

The system 100 may be in electrical communication with a plurality of remote care facilities 104 via the network 114, as shown in FIG. 1. The remote care facilities can include a destination in-network hospital 117 for repatriation of an admitted out-of-network patient. Additionally remote care facilities can include a long-term facility 116, a sub-acute facility 118, a skilled nursing facility 120, and home care 122. Insurance companies 126 (and/or independent physicians associations (IPAs)) may likewise be in communication with the system 100 via the network 114. Web server 136 may be connected to the system 100 via the network 114 to provide a web site with a plurality of user interfaces as described in more detail below.

One function of the system server 110 is to serve as a conduit for the transmission of messages (1) between the portable data entry terminals 106 and any of the remote care facilities 104, or (2) for messages generated by the system server 110 and automatically transmitted to one of the remote care facilities 104 that is, for example, a physician 124 carrying a mobile communications device 125 or a managed care provider/insurance payer 126 as shown in FIG. 1. Each of these types of messages can be transmitted to the recipient remote care facility 104 via a network 114 as shown in FIG. 1. The system server 110 can be in physical communication with the network 114 as is shown in FIG. 1. The network 114 may operates in a secure, online interactive mode in cyber communication with the system server 110 and the remote care facilities 104 for enabling access to the data stored in the system data storage memory 112 and for serving as a communications conduit. The entered and stored data can be accessible from both the portable data entry terminals 106 and the remote care facilities 104 with the use of a password once the transfer of the patient case has been offered to the particular remote care facility 104. This facilitates access by the remote care facility 104 to the entered medical data stored in the system data storage memory 112 for the purpose of evaluating the patient. Furthermore, cyber communications between the remote care facilities 104 and the portable data entry terminals 106 over the network 114 operating in a secure online interactive mode facilitates the placement of the patient in one of the remote care facilities 104 upon discharge of the patient from the acute-care hospital environment or repatriation of the patient from an out-of-network admitting hospital to an in-network destination hospital. A suitable example of the network 114 is the system known as the Internet.

Each of the remote care facilities 104 can be physically connected to the network 114 as shown in FIG. 1. Each of the remote care facilities 104 represents one of a plurality of different level care facilities that is licensed to provide a certain level of convalescing care for a patient discharged from the acute-care hospital environment. Destination hospital 117 represents a hospital associated with another insurance network, allowing for repatriation for admitted out-of-network patients to in-network destination hospital 117. The long term care facility 116 can be licensed to provide long term acute care to patients who exhibit stable clinical values but continue to remain in serious condition although they do not need to be hospitalized. Stable clinical values include readings within the normal range for body temperature, blood pressure, heart rate, respiration rate, and laboratory and culture results. Typically, there is a medical staff present at all times. Unlike other remote care facilities 104, long term care facilities 116 can accept patients who, for example, are mildly agitated and/or restrained or are fitted with feeding or breathing tubes. A sub-acute care facility 118 is a remote care facility 104 that ranks below a long term care facility 116. The sub-acute care facility 118 is licensed to provide less than acute convalescing care to patients who exhibit stable clinical values and who do not require hospitalization or who are not required to be in a long term care facility 116. Typically, there is a medical staff present with doctors on-call. The sub-acute care facility 118 may not admit a patient that is agitated and/or restrained or those that are fitted with feeding or breathing tubes.

A skilled nursing care facility 120 is a remote care facility 104 that ranks below a sub-acute care facility 118. The skilled nursing care facility 120 is licensed to provide convalescing care at a care level below that of the sub-acute care facility 118. Patients who are candidates for discharge to a skilled nursing care facility 120 do not require hospitalization, or acute convalescing care, and are sufficiently recovered so that they do not require the presence of a medical doctor. Typically, the medical staff is comprised of registered and licensed practical nurses but medical doctors can be available, if necessary. Home health care 122 is the lowest care level of the remote care facilities 104. Patients who are candidates for home health care 122 are those patients that have essentially recovered from their condition but still need periodic medical attention, such as from a licensed practical nurse. An example of such a patient might be one who has experienced an orthopedic surgery on, for example, a knee joint. Under these conditions, the patient can be discharged from the acute care hospital environment directly to her residence. Then, on a periodic schedule, a licensed practical nurse or physical therapy specialist can visit the patient at her residence for consultation or outpatient treatment until the patient has completely recovered.

The system also includes a system web server 136 and is shown in FIG. 1 as being in communication with the network 114. The system web server 136 can be in communication with the network 114 to facilitate contact with all third parties. Consequently, all computers connected to, for example, the Internet can access the system web server 136 to obtain information uniquely associated with the system 100. Any third party can access the system web server to obtain general information but a password may be required to access certain confidential sections such as, for example, patient records including the Daily Nursing Report and the Daily Case Management Report. Consequently, hospital administration, medical doctors, and the nursing staff would be assigned a password to access the confidential sections of the system web server 136. Furthermore, under certain situations, a particular remote care facility or facilities 104 would be temporarily assigned a password at the time the acute care hospital offered to discharge or repatriate a patient to that remote care facility 104 so that the remote care facility 104 could access the patient's medical reports. This access would enable the remote care facility 104 to evaluate the patient's medical history and condition to determine if that particular remote care facility 104 was the best suited facility to which the patient should be discharged or repatriated to. Under other conditions, the hospital could temporarily assign a password to a patient or the patient's family for providing online access to educational modules or virtual visit videos (not shown) for reviewing and subsequently entering the preferred remote care facility 104 to which the patient should be discharged or repatriated. To accomplish this, the system web server 136 can communicate with the system server 110 and the system data storage memory 112, for example, over a wireless link 138, as shown in FIG. 1. Additionally, other hospital computers 140 shown in FIG. 1 can access the system web server 136 over the wireless link 134 and can be employed to communicate with any of the remote care facilities 104 in cyber communication with the network 114.

Each of the physicians 124 associated with the case management system 100 treats patients whose medical data can be wirelessly transmitted to the system server 110 and stored in the system data storage memory 112. The nursing staff monitors the clinical parameters such as, for example, body temperature, blood pressure, respiratory rate and the like, of the patients on a daily basis. These daily readings of clinical parameters are wirelessly transmitted to the system server 110 from the data entry terminals 106. When certain clinical parameters reach a threshold value, the physicians attending these patients wish to be contacted with this clinically sensitive information. Computer program or software within the system server 110 has been programmed to identify these threshold clinical values and treat them as a condition precedent to some action. The condition precedent might be satisfied when the body temperature of the patient reaches 102.4 degrees Fahrenheit. Under these conditions, the physician 124 might wish to be contacted so that some further action might be taken such as, for example, administering an alternative medication. The physician 124 might not wish to be notified for every change in the patient's condition. Thus, the computer program software associated with the system server 110 can include both (1) a "general menu" of orders, and (2) a "personalized menu" of orders of what the physician 124 wishes to be informed about, i.e., the clinically sensitive issues.

Thus, not only will the case management system 100 be capable of audio/text messaging clinical sensitive case information regarding clinically sensitive issues but it will also have the capability to be "specialty specific". For example, if an infectious disease physician 124 (physician #1) is involved in the patient's case, he will have an identifying code entered onto that patient's medical file. The physician 124 will be able to request that certain clinical information be brought to his attention promptly. Likewise, other clinical information that he does not need to know about right away does not need to be audio/text messaged to him. The "general menu" will include, for example, what most other infectious disease physicians 124 want to know such as, for example, positive culture results, high fever and the like. In another example, a cardiologist (physician #2) might want to know information related to the patient's heart rhythms or blood pressure increases, or positive troponin levels (which are laboratory levels that if positive, indicate that the patient is suffering a heart attack). In the alternative, the physician's "personalized menu" can include items requested by the physician 124 (physician #1) that contain certain clinical states or laboratory results that will be audio/text messaged to the physician 124. Likewise, the physician 124 may instruct that other items listed on the physician's "personalized menu" not be audio/text messaged to him. Further, the menus can also include reference referral information specifying the identity of a consulting physician (physician #2) on other related matters concerning the patient being treated by the physician 124 (physician #1). The consulting physician (physician #2) would typically be a physician 124 practicing a specialty (such as cardiology) other than the specialty (such as infectious diseases) practiced by the attending physician 124 (physician #1). Consequently, the case management system 100 can be capable of being "specialty specific" by identifying and transmitting the clinically sensitive case information to physician #1 (the infectious diseases doctor) verses physician #2 (the cardiologist) depending on what information is listed on their "general menu" versus the "personalized menu".

In order to address this need, embodiments of the system include a feature identified as the Automated Physicians Assistant which functions to automatically notify the physician 124 when the programmed software of the system server 110 recognizes that the threshold value of a clinical parameter has been reached. The computer software can be programmed to automatically instruct the system server 110 to transmit a signal across the network 114 typically to a mobile communications device 125 carried by the physician 124. The mobile communications device 125 can be in signal communication with the network 114 as shown in FIG. 1. The signal automatically transmitted from the system server 110 to the mobile communications device 125 serves to indicate to the physician 124 that the threshold condition has occurred and that the data associated with that measured clinical value has been entered into the system data storage memory 112. The signal transmitted by the system server 110 can include audio beeps or text messaging and be "specialty specific" directed to one or more physicians 124 practicing in a relevant medical specialty. Furthermore, the subject matter of the text message can include information listed on the physician's "general menu" or on the "personalized menu" related to clinical data from a certain medical case.

The Automated Physicians Assistant may operate in the following manner. The computer software of the system server 110 can be programmed to automatically contact the mobile communications device 125 carried by the physician 124 as soon as a certain threshold parameter exists. No human intervention or telephone calls are required. The case management system 100 recognizes that the threshold condition precedent has occurred and automatically notifies the physician 124. For example, as soon as a laboratory culture result for the patient is determined, the data can be entered into the system data storage memory 112 of the system server 110 by, for example, laboratory personnel. If the laboratory result matches or exceeds the threshold value and the threshold value of that parameter is listed on the physicians "general menu" or "personalized menu", the system server 110 can be programmed to automatically send a signal to the mobile communications device 125 carried by the physician 124. The signal can be audible and advises the physician 124 to check his e-mail, voice mail, system instant text messaging, or to contact the staff nurse or laboratory tech. The mobile communications device 125 carried by the physician 124 can be a cell phone, a smartphone, pocket PC or other device that can be wirelessly connected to the network 114.

Another method by which a third party can communicate with the physician 124 of a patient is by use of third party tele-messaging. A third party such as a nurse or a laboratory technician decides that they must communicate with the physician 124 regarding a patient condition that is not entered into the system data storage memory 112. Thus, this patient condition is not transmitted to the physician 124 via the Automated Physician's Assistant. The nurse can send the message to the physician 124 from one of the portable data entry terminals 106 (that is, on one of the notebook computers) or, in the alternative, from a 3rd party computer or one of the other hospital computers 140 as is shown in FIG. 1. All communications between the hospital staff and the physician 124 taking place on the case management system 100 are always routed through the system server 110. The message sent by the nurse can be recorded on the system server 110 and the computer software can be programmed to send a text message or audible beep to the mobile communications device 125 carried by the physician 124. The physician 124 can then take appropriate action by accessing the system server 110 using his assigned secure password either by using her mobile communications device 125 or by using a third party or hospital computer 140, or in the alternative by telephoning the nurse that sent the original message. Either of these methods will enable the physician 124 to successfully access the message stored on the system server 110. Another example might include the scenario in which the tele-message can be transmitted from the acute care hospital 102 to, for example, one of the remote care facilities 104 announcing the impending discharge or repatriation of a patient and seeking an admissions response.

Another feature enables the computer program to automatically instruct the system server 110 to recognize a secure password transmitted to the system server 110 over the network 114 from one of the remote care facilities 104. This enables the remote care facility 104 to gain access to the data stored in the system data storage memory 112 so that the medical condition of the patient can be investigated. In some embodiments, the only data entered into the system data storage memory 112 is the data entered by hospital personnel including the staff nurses and hospital administration. This includes information provided by the remote care facilities 104 regarding bed availabilities. This accumulated information can then be used by hospital personnel to formulate a daily discharge information list, patient data information in placement of discharged patients in remote case facilities 104, and to assist physicians 124 with patient management. However, there are times when third parties including the remote care facilities 104 must gain access to the data stored in the system data storage memory 112. One of those times is when the hospital personnel offers a patient referral to one of the remote care facilities 104. The remote care facility 104 can then have access to the medical reports available on the system server 110 with password access such as, for example, the Daily Nursing Report and the Daily Case Management Report to evaluate the patient's condition. The patient's condition can be evaluated so that the remote care facility 104 can determine if they have the professional capability, facilities, personnel and bed availability to accommodate the soon-to-be-discharged patient. The remainder of the clinical data and reports needed by the remote care facility 104 to evaluate the patient's condition can be scanned into the hospital scanner 130 and electronic-facsimile transmitted (i.e., e-faxed) to the remote care facility 104 for review.

The governing Act that sets the security standards as it relates to the electronic transmission of patient medical information is the Health Insurance Portability and Accountability Act of 1996 (Public Law 104-191) enacted by the 104th Congress and is referred to as HIPAA. The Act is directed to online Federal security legislation and includes a section directed to medical privacy setting forth National Standards to Protect the Privacy of Personal Health Information. Under these guidelines, standard e-mail transmission of patient medical information such as clinical data and reports is not permitted since that mode of transmission fails to meet the rigid confidentiality requirements. That is, standard e-mail transmission is not sufficiently secure and can be accessed by parties outside of the case management system 100. Consequently, patient medical information is typically transmitted by electronic facsimile transmission, or "e-fax", which is more secure against outside intrusion.

A further feature involves a specific remote facility 104, in particular, the insurance company 126. This feature is incorporated into the computer program or software of the system server 110 to provide the insurance company 126 access to the daily patient clinical data/information stored in the system data storage memory 112 and to patient case management forms. In the past when a patient was admitted to the acute hospital environment, case managers working for the insurance company 126 were charged with the responsibility of determining if the patient carried a valid insurance policy with the insurance company 126, and what the limitations and parameters of the policy were. Additionally, the insurance company 126 developed criteria profile to decide if the patient was authorized to be hospitalized. It was the insurance company case manager's responsibility to ensure that the criteria profile for an authorized hospitalization was satisfied before the insurance company 126 would agree to reimburse the acute care hospital 102 for any of the patient's bills. Typically, once the hospitalization was approved, the insurance company 126 would authorize blocks of three-to-four days at a time for patient treatment and reimbursement of costs, expenses and charges. This task was typically accomplished by hand since the entire system was not computerized in the prior art.

In the past, this function was accomplished by the insurance company 126 by employing thousands of case managers who reviewed the clinical information of their insured hospitalized patients either daily or every other day. This task was typically accomplished by the case managers of the insurance company 126 by collecting the necessary clinical information either by telephone or facsimile transmission from the case managers at the acute hospital environment.

Thereafter, the case managers of the insurance company 126 would compare the clinical information for each insured hospitalized patient to the insurance company criteria profile to determine whether the insurance company will either authorize or deny payment or refer the patient matter to a medical review board to decide if payment is authorized. This process is typically practiced by each of the four main managed care providers/insurance companies 126 in the industry today.

The insurance company 126 is treated in a similar manner as the remote care facilities 104. This is accomplished by providing the insurance company 126 access to the daily clinical information collected and entered into the data entry terminals 106 by the nurse and wirelessly transferred to the system data storage memory 112 as shown in FIG. 1. Much like the remote care facilities 104, the insurance company 126 can be provided with a suitable password for gaining access to the system data storage memory 112 of the system server 110. This password will enable personnel at the insurance company 126 to access data and download the Daily Nursing Report and the Daily Case Management Report to evaluate the patient's condition. This process, in turn, will enable the insurance company 126 to determine if the patient subscribes to a valid medical insurance policy and whether hospitalization of the patient will be authorized. Further, the insurance company will be able to automatically authorize "days" of hospitalization that they will approve for reimbursement instead of blocks of days. This improves system efficiency by limiting the time a patient spends in the hospital environment. This procedure can be accomplished online in minutes instead of having to spend extended time periods on the telephone or sending facsimile transmissions as in the past.

The criteria profile developed by the insurance company 126 to determine whether the patient is an insured of the insurance company 126, what the policy limitations are, and whether the policy is enforceable is now programmed into the computer program or software of the system server 110. Further, recall that the clinical data entered daily into the data entry terminals 106 by the nurse during her early morning visits to each patient can be wirelessly transferred to the system server 110 and stored in the system data storage memory 112. Consequently, the computer program or software of the system server 110 compares the clinical data stored daily in the system data storage memory 112 with the criteria profile of the insurance company 126. This comparison occurs automatically to determine the existence and limitations of a insurance policy. More importantly, the computer program comparison automatically authorizes or denies reimbursement to the acute care hospital 102 for that day or, in the alternative, refers the case for decision to a medical review panel within the insurance company 126. Further, a determination can be made as to whether the remote care facility 104 is capable of caring for the patient upon discharge from the acute care hospital 104 and whether there is a bed available for the patient suffering from a certain ailment. This is a function of the case manager of the insurance company 126. This design eliminates the requirement of the ongoing telephone conferences and facsimile transmission exchanges between the case managers of the acute care hospital 102 and the case managers of the insurance company 126 regarding reimbursement authorization approvals and denials. As can be seen from the foregoing, the case management system 100 not only emulates the duties and performs the function of the case managers of the acute care hospital 102 but also emulates the duties and performs the function of the case managers of the insurance company 126 as well. This novel feature represents a significant advance over the capabilities of prior art systems.

It is emphasized that authorized personnel of the insurance company 126 using the password assigned in accordance with the case management system 100 may be able to access the Daily Nursing Report and the Daily Case Management Report on the system website. This access provides the personnel of the insurance company 126 the ability to download the electronic files for specific patients for use in making financial reimbursement decisions. An additional method available to the insurance company 126 to track a particular patient is to audit the patient's electronic file. For example, the insurance company 126 can download one of the reports online and then record that report on some recordable media such as, for example, a diskette. Then the media recorded onto the diskette can be audited for a quality control check regarding authorizing or declining reimbursement of an item charged by the acute care hospital 102. Further, this procedure provides for a daily check by the insurance company 126 as to the whereabouts of their patients. In particular, the insurance company 126 can be notified electronically by the acute care hospital 102 when the patient can be admitted along with specific admission information. This notification enables the insurance company 126 to make decisions such as, for example, (1) whether the patient should be admitted at all specifically referring to the patient's clinical criteria such as vital signs, symptoms, laboratory values, blood pressure, and the like, and (2) whether the patient's insurance policy covers the specific acute care hospital 1021 claimed benefits, and the like. Additionally, the computer program or software of the system server 110 can be pre-programmed to include the list of benefits included in the patient's medical insurance policy. This feature benefits the acute care hospital 102 since the acute care hospital 102 also has access to the system server 110 via an assigned password. Thus, the acute care hospital 102 can determine what benefits the patient has upon admission. Consequently, the insurance company 126 benefits since the acute care hospital 102 does not have to communicate with the insurance company 126 via telephone or facsimile transmission to verify the benefits of the patient. Furthermore, the preprogramming of the list of patient's benefits in the system server 110 also eliminates human error during these communications, Another feature is directed to electronic billing for services rendered. After the patient treatment program has terminated, the financial records associated with the treatment program enables the generation of a billing statement by the computer program of the system server 110. The billing statement would list reimbursement charges for those hospitalization days that were authorized by the insurance company 126. The generated billing statement would be transmitted from the acute care hospital 102 to the appropriate managed care provider or insurance company 126 for reimbursement of expenses and charges associated with treating the patient. The billing statements can be transmitted in electronic format or as a paper document. Likewise, billing statements can be generated for presentation to other medical insurance plans such as, for example, the California State Medi-Cal program or the Federal Medicare program. All of the information required to generate a billing statement for either the state or federal medical programs can be included in the original data collected daily by the staff nursing personnel and entered into the data entry terminals 106 and wirelessly transmitted to the system server 110.

Repatriation Management System

Patients are often admitted to hospitals which are not covered, or not fully covered by the patients' insurer. This can be particularly true in the case of emergencies, in which case the patient is often taken to the most convenient hospital, irrespective of the patient's insurance status. However, costs accrued by the patient during her stay in an out-of-network hospital risk going unpaid if the patient's insurer does not cover them, and the patient herself is unwilling or unable to make payment. Accordingly, once such a patient is sufficiently medically stable, it is often desirable to transfer the patient from the out-of-network hospital to which she has been admitted, to an appropriate in-network hospital. This process is referred to herein as "repatriation". In order to repatriate patients from out-of-network to in-network hospitals or other medical facilities, a great deal of planning often takes place, involving numerous back-and-forth communications between a case worker at the admitting hospital, staff at the destination hospital, and medical transport providers, often involving a number of telephone calls and fax communications of voluminous patient data. A case worker assigned to the patient typically begins the repatriation process as soon as it is discovered that the patient's insurer does not cover, or does not fully cover, services are the admitting hospital. There is often a significant delay before the hospital staff becomes aware of this, and the patient's insurer often is not informed until even later. In order to manage the repatriation process, the case worker typically makes telephone calls and/or faxes requests to one or more in-network hospitals, including voluminous patient information. The case worker must then wait for responses, and then arrange transport for the patient once an in-network hospital has agreed to accept the patient.

Figure 2:
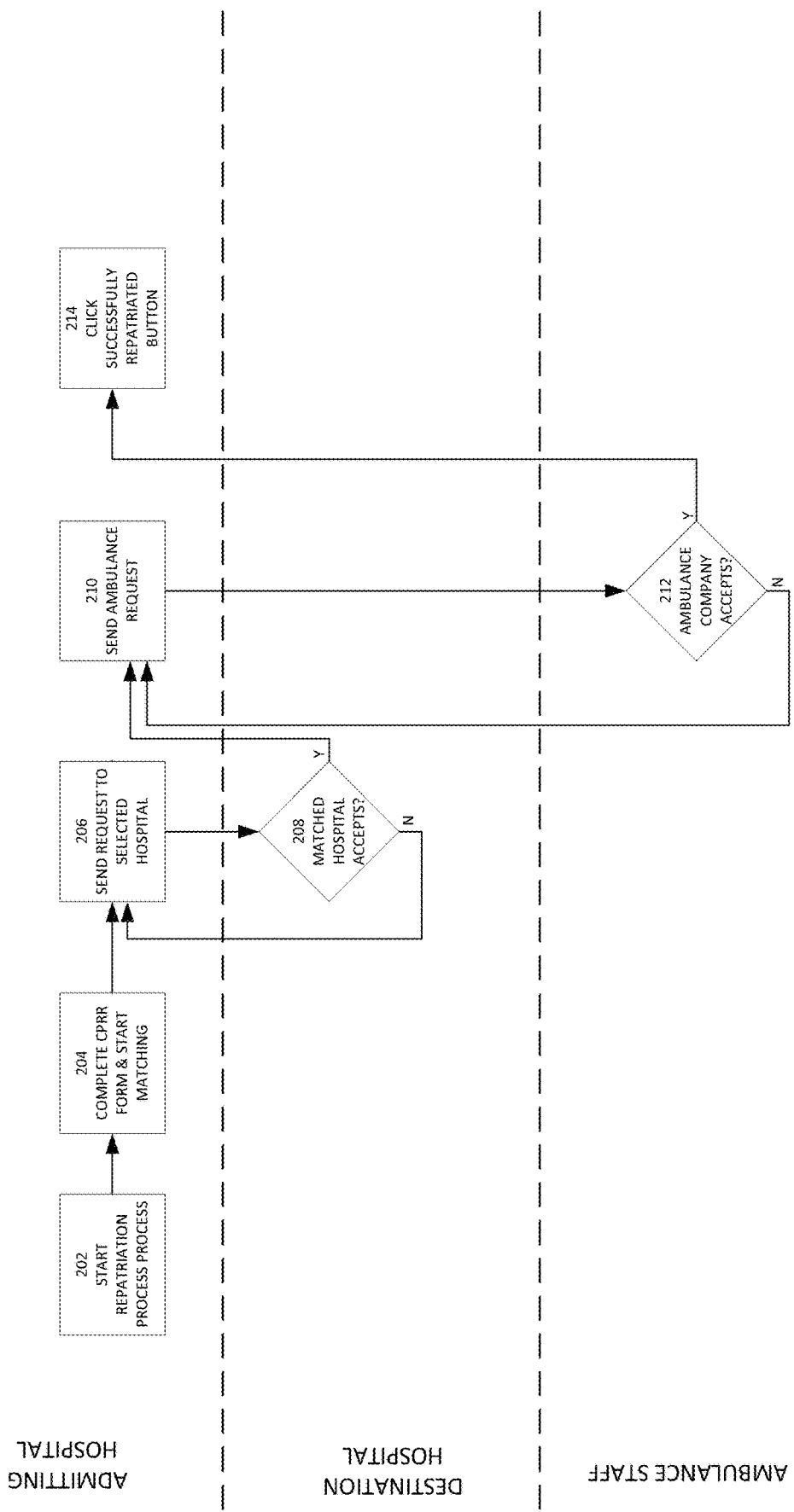
FIG. 2 illustrates an example process for repatriation management.

FIG. 2 illustrates an example process for repatriation management. The process flow outlines communication between three separate entities: the admitting hospital, the destination hospital, and ambulance staff. In use, this process may provide for communication between multiple entities in parallel, as described in more detail below. For example, the admitting hospital may send requests to a number of different candidate destination hospitals, and each candidate destination hospital may in turn receive a number of requests for a given number of beds. Likewise, ambulance staff may both receive initial requests for a number of patient transports from a variety of admitting hospitals, and the admitting hospital may send ambulance requests to any number of different ambulance companies or other medical transport providers. The process begins with the admitting hospital in which a patient, who is typically associated with an insurer that is not associated with the admitting hospital (i.e., the patient is "out-of-network" at the admitting hospital). In some cases, the patient may be admitted to the admitting hospital in the case of an emergency, which case the repatriation process begins only when the patient has been deemed sufficiently medically stable to be transported to an "in-network" hospital.

Staff at the admitting hospital, for example a case manager, may begin the process in block 202 with initiating the repatriation process. In block 204, a clinical profile request for repatriation (CPRR) form is completed electronically, for example via a graphical user interface at a user terminal in the admitting hospital, via a mobile device carried by the hospital staff, or otherwise. The repatriation request form may include relevant clinical and biographical patient data, including for example patient insurance, required medications, required equipment (e.g., breathing machine, dialysis, etc.), level of staff care, any need for isolation for example due to infection, etc. In some embodiments, the repatriation request form may be automatically populated with patient clinical and biographical data, for example by pulling information from electronic medical records on other hospital computer systems. In some embodiments, the case manager can use a QR or barcode scanner to scan a code associated with the patient, for example a code affixed to the patient's ID card, wrist band, etc. Scanning the QR code or barcode can initiate a call to patient data previously saved in the system, which can be used to populate the CPRR form. Once the CPRR form is completed, the case manager or other admitting hospital staff can initiate matching of candidate destination hospitals. In some embodiments, the repatriation management system analyzes the patient clinical data and the previously stored data regarding a number of candidate destination hospitals. The system matches the patient to all candidate destination hospitals meeting the specified criteria. For example, depending on the patient's insurance status, clinical information, and the required level of care, the repatriation management system may compute matches to one or more candidate destination hospitals.

In block 206 the case manager can send requests to a selected destination hospital from among the list of candidate destination hospitals provided by the system. In some embodiments, a list of matching candidate destination hospitals computed by the repatriation management system can be displayed to the case manager, for example via a graphical user interface on a computer terminal or mobile device. The case manager can select from among the listed candidate destination hospitals and choose to send requests to one or more. In some embodiments, the case manager may initiate requests to several different candidate destination hospitals in parallel.

Block 208 illustrates action on behalf the selected destination hospital. As noted above, in some embodiments a number of different candidate destination hospitals can each receive requests in parallel for repatriation of the same patient. The description herein relates to the actions and interactions for a single destination hospital, but it will be understood that in other embodiments the process can happen in parallel across many candidate destination hospitals. In block 208, the selected destination hospital receives a request for repatriation of a particular patient. The request can be received, for example, via a graphical user interface accessed on a computer terminal or mobile device. In some embodiments, the graphical user interface is provided via a network connection to the repatriation management system, for example via a web portal that is separately accessible by the separate entities. By securely logging into such a web portal, each entity may be provided with a different set of graphical user interfaces as needed. For example, in block 208, the destination hospital may see a list of incoming repatriation requests. By selecting one of the requests, the destination hospital staff may access additional information regarding the patient, for example insurance information, medical condition, required medication, and so forth. The destination hospital has the option of either accepting the request, if they have determined that they are at least interested in accepting the patient. The destination hospital may conversely determine that they do not wish to accept the patient, for example due to space restrictions, concerns over insurance, medical condition, or otherwise. Should the destination hospital decline the request, the admitting hospital staff will be notified, for example via the web portal, and the admitting hospital may initiate additional repatriation requests as needed. In some embodiments, the admitting hospital will have previously submitted to multiple candidate destination hospitals, and so upon receiving a notification that one of the candidate destination hospitals has declined, the admitting hospital will simply look to other candidate destination hospitals to which it has transmitted requests. Should the destination hospital send an acceptance, the admitting hospital will be notified, for example via the web portal.

In block 210, a request for medical transport, such as an ambulance, is sent by the admitting hospital. In some embodiments, the admitting hospital staff may view confirmation of final acceptance from the destination hospital, for example via a web portal, and may click a button or otherwise initiate the ambulance request. In some embodiments, a list of possible ambulances or other medical transport provides can be displayed to the admitting hospital staff, and one or more of those ambulances can be selected for transmission of a transport request. In some embodiments, the repatriation management system may automatically communicate the transport request to all identified ambulances or medical transport providers. In some embodiments, the system may limit those ambulance providers to whom the request is sent based on a number of different criteria. For example, the system may limit the ambulance providers based on insurance status (e.g., only request ambulance providers associated with the patient's insurer), medical condition (e.g., only request ambulance providers with adequate capability to transport the patient given the medical condition), or other factor. In some embodiments, the repatriation management system may automatically contact the insurer associated with the patient and one or more of the ambulance providers, to obtain authorization for the transport. This can provide the patient and the medical transport providers with the confidence that costs for the transport will be reimbursed by the insurer.

In block 212, action on behalf of one of the ambulance providers is illustrated. As noted above, in some embodiments a number of different ambulance providers can each receive requests in parallel for transport of the same patient. The description herein relates to the actions and interactions for a single ambulance provider facility, but it will be understood that in use the process can happen in parallel across many ambulance providers. In block 212, the ambulance provider receives a request for transport of a particular patient from the admitting hospital to the selected destination hospital. The request can be received, for example, via a graphical user interface accessed on a computer terminal or mobile device. In some embodiments, the graphical user interface is provided via a network connection to the repatriation management system, for example via a web portal that is separately accessible by the separate entities. By securely logging into such a web portal, each entity may be provided with a different set of graphical user interfaces as needed. For example, in block 212, the ambulance provider may see a list of incoming transport requests. By selecting one of the requests, the ambulance provider staff may access additional information regarding the patient, for example insurance information, medical condition, required medication, and so forth. The ambulance provider then has the option of either accepting or declining the request. Should the ambulance provider decline the request, the admitting hospital staff will be notified, for example via the web portal, and the admitting hospital may initiate additional transport requests as needed. In some embodiments, the admitting hospital will have previously submitted to multiple ambulance providers, and so upon receiving a notification that one of the ambulance providers has declined, the admitting hospital will simply look to other ambulance providers to which it has transmitted requests. Should the ambulance provider send an acceptance, or "bid" on the transport request, the admitting hospital will be notified, for example via the web portal.

In some embodiments, the admitting hospital may receive acceptances or bids from a number of different ambulance providers, in which case an additional step of selecting from among the accepting ambulance providers may be undertaken by the admitting hospital. In such embodiments, upon selecting of the final ambulance provider for transport, the non-winning bidders (i.e., ambulance providers who accepted the request, but were not selected for final transport by the admitting hospital) will be notified automatically, for example via the web portal. Finally, in block 214, once the patient has been picked up by ambulance staff, the admitting hospital may select a "successfully repatriated" button or otherwise indicate that repatriation has been completed. The repatriation management system may automatically provide this indication to any number of other entities, for example the patient's insurer, non-selected candidate destination hospitals, non-selected ambulance providers, and other staff at the admitting hospital.

Figure 3A:
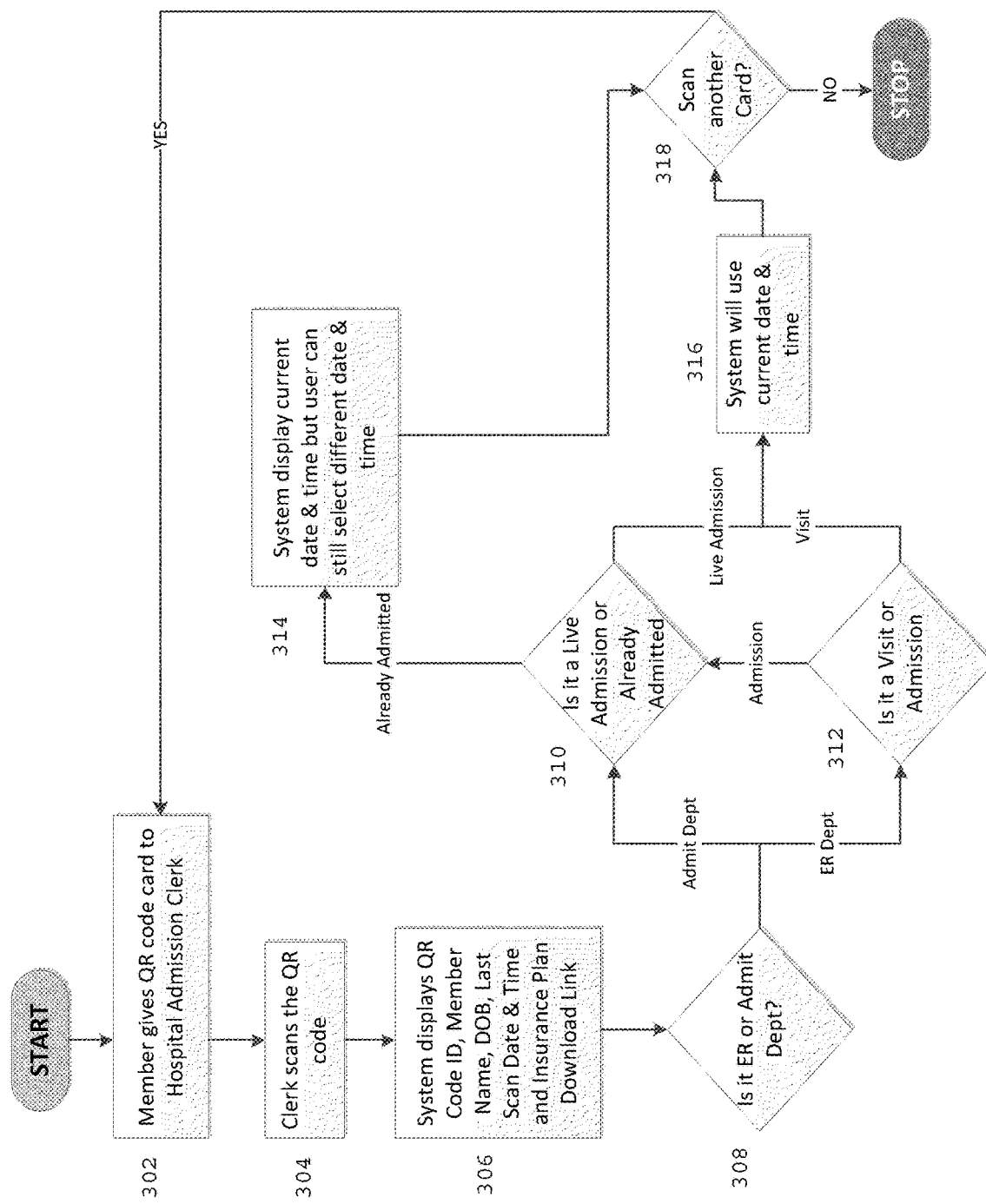
FIG. 3A illustrates an example intake process for repatriation management.

FIG. 3A illustrates an example intake process for repatriation management, and FIGS. 3B-3H illustrate example user interfaces which may be displayed to different entities throughout different points in the process. In block 302, a member, for example a patient being admitted to the admitting hospital, can provide her QR code card to a hospital admission clerk. In some embodiments, the member may have a QR code affixed to her insurance ID card, or other identification card. In other embodiments, the member may have a dedicated card for the QR code. In some embodiments, the QR code can be replaced with a bar code, serial number, or other such identification technique.

Figure 3B:
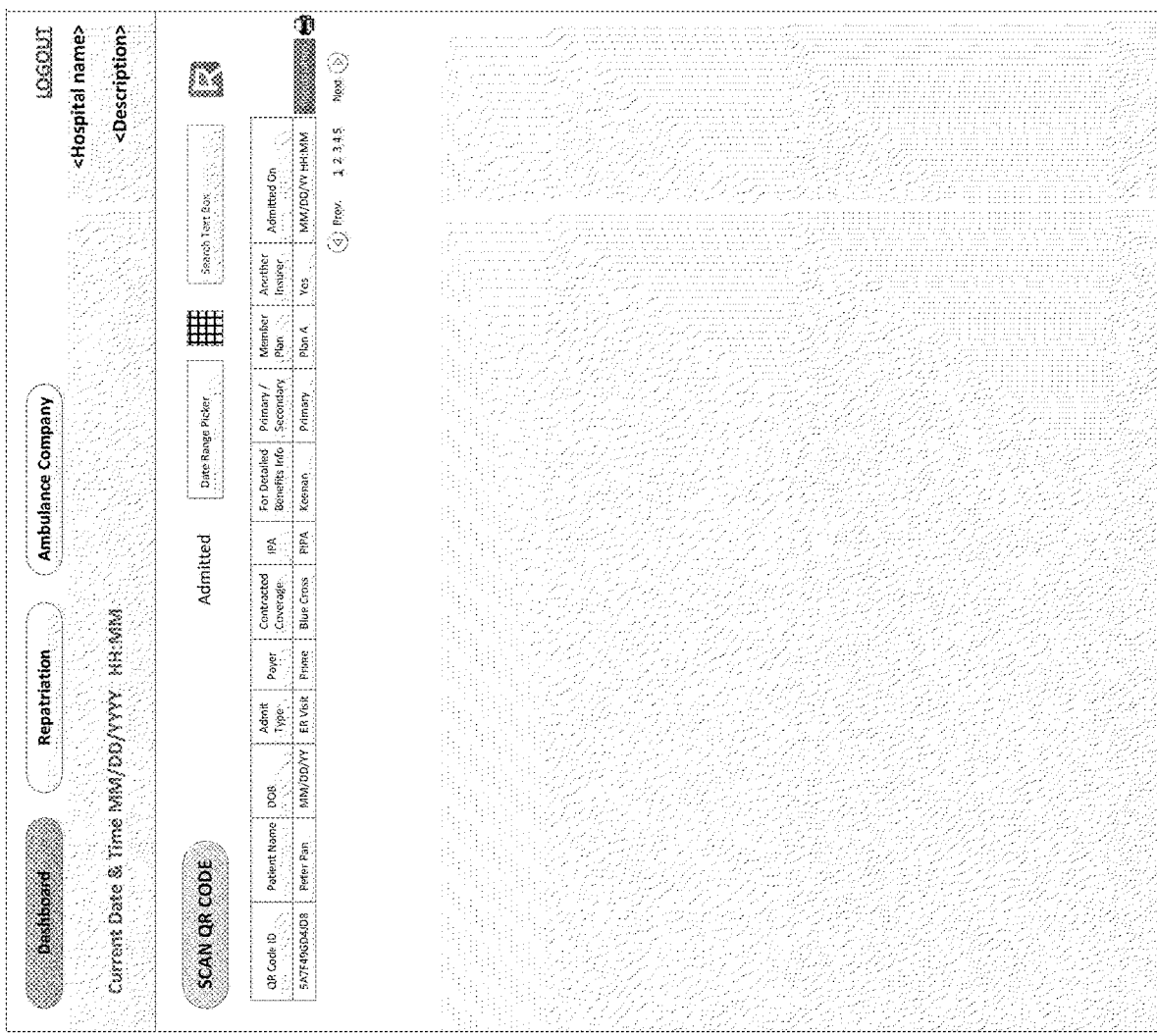
FIGS. 3B-3G illustrate example user interfaces.
Figure 3C:
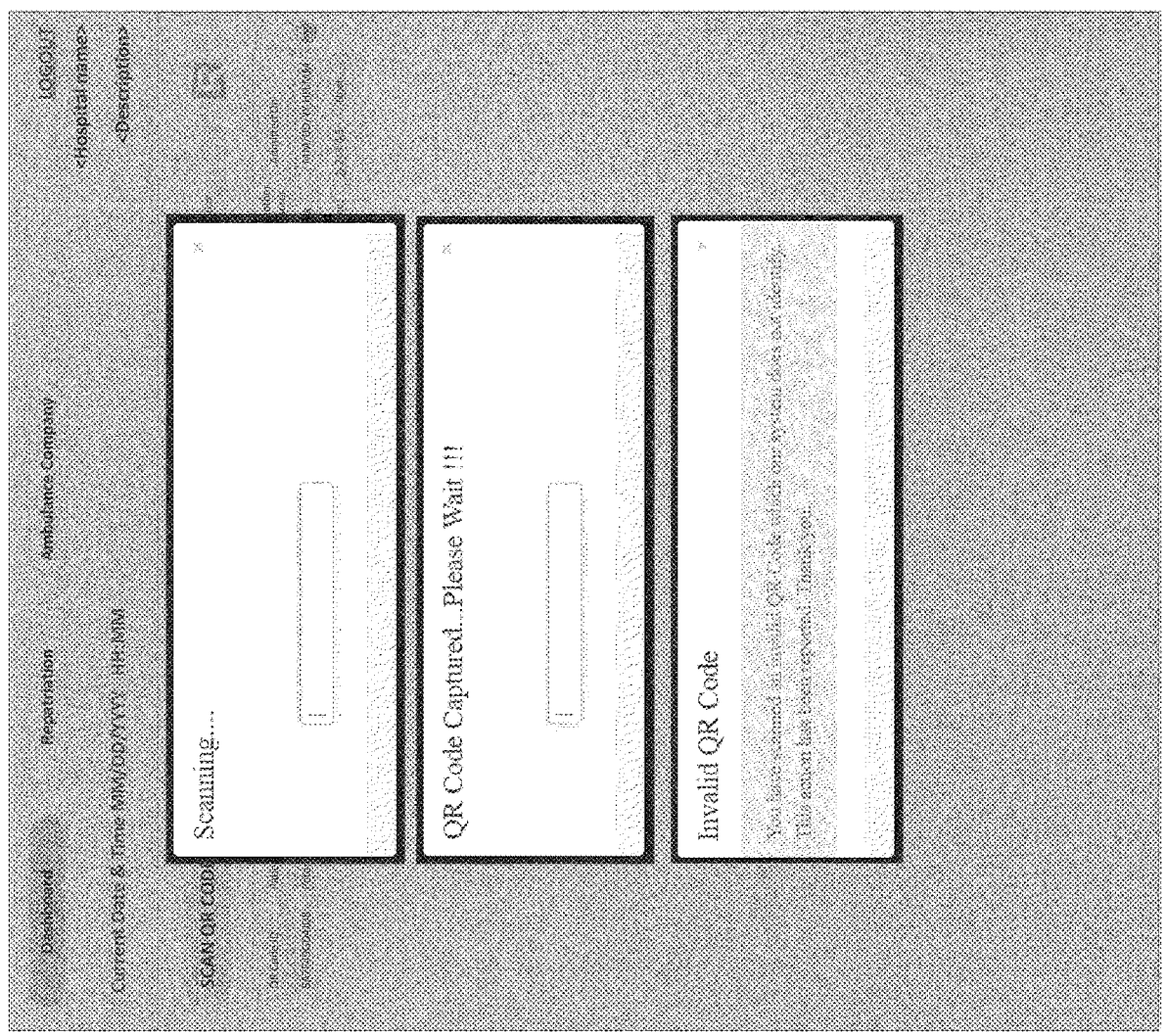

The hospital admission clerk may access the repatriation management system via a graphical user interface, for example through a secure web portal. As shown in FIG. 3B, a dashboard can be displayed to the hospital clerk, with a button labeled "SCAN QR CODE". Upon selecting this button, the interface shown in FIG. 3C is displayed as a pop-up. The uppermost pop-up box shown in FIG. 3C may be displayed upon clicking the "SCAN QR CODE" button. Then, in block 304, the clerk scans the member's QR code. In response, the middle pop-up box of FIG. 3C can be displayed. In the event that the QR code was invalid, the lowermost pop-up box of FIG. 3C can be displayed to the hospital admission clerk.

Figure 3D:
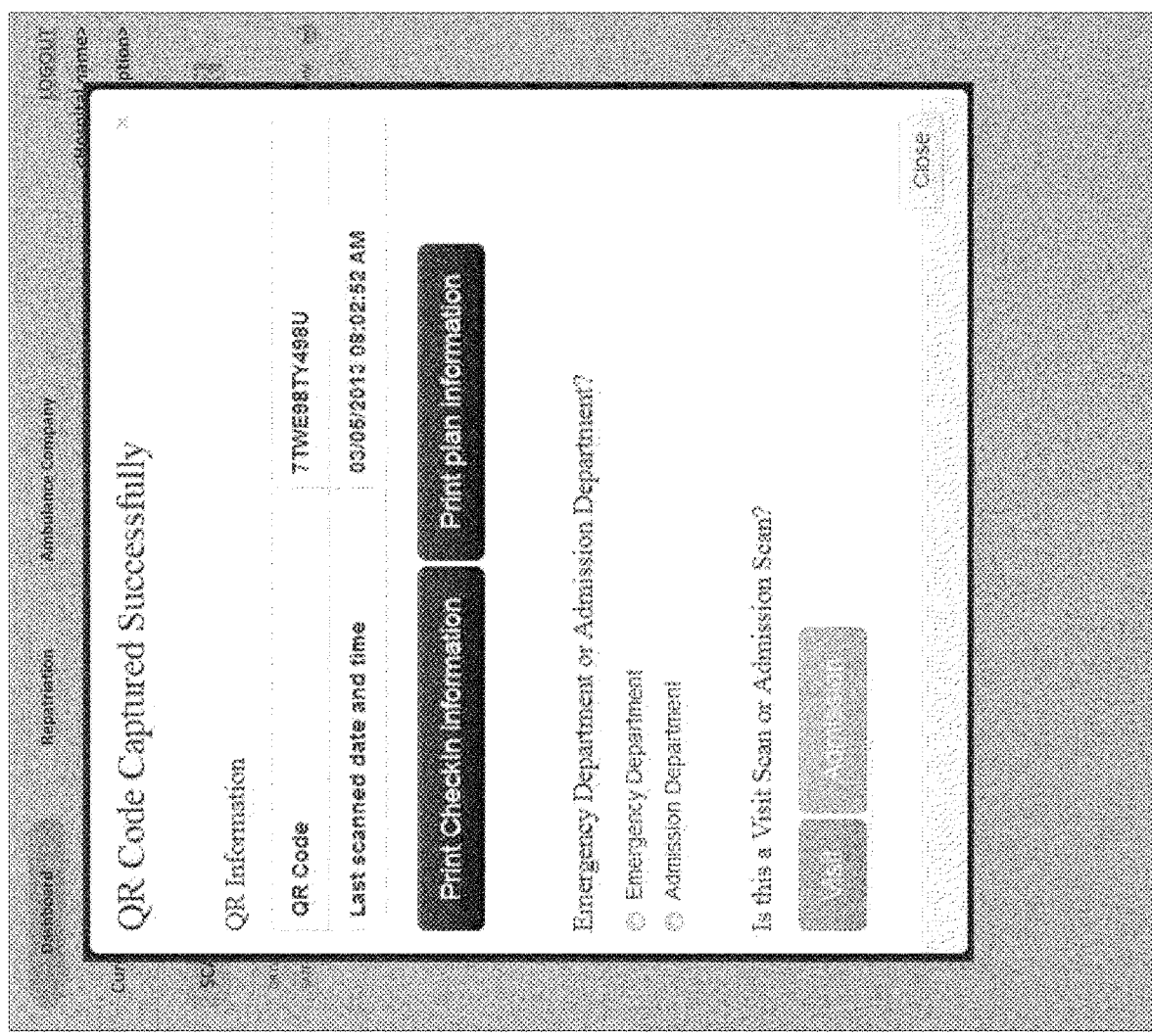
Figure 3E:
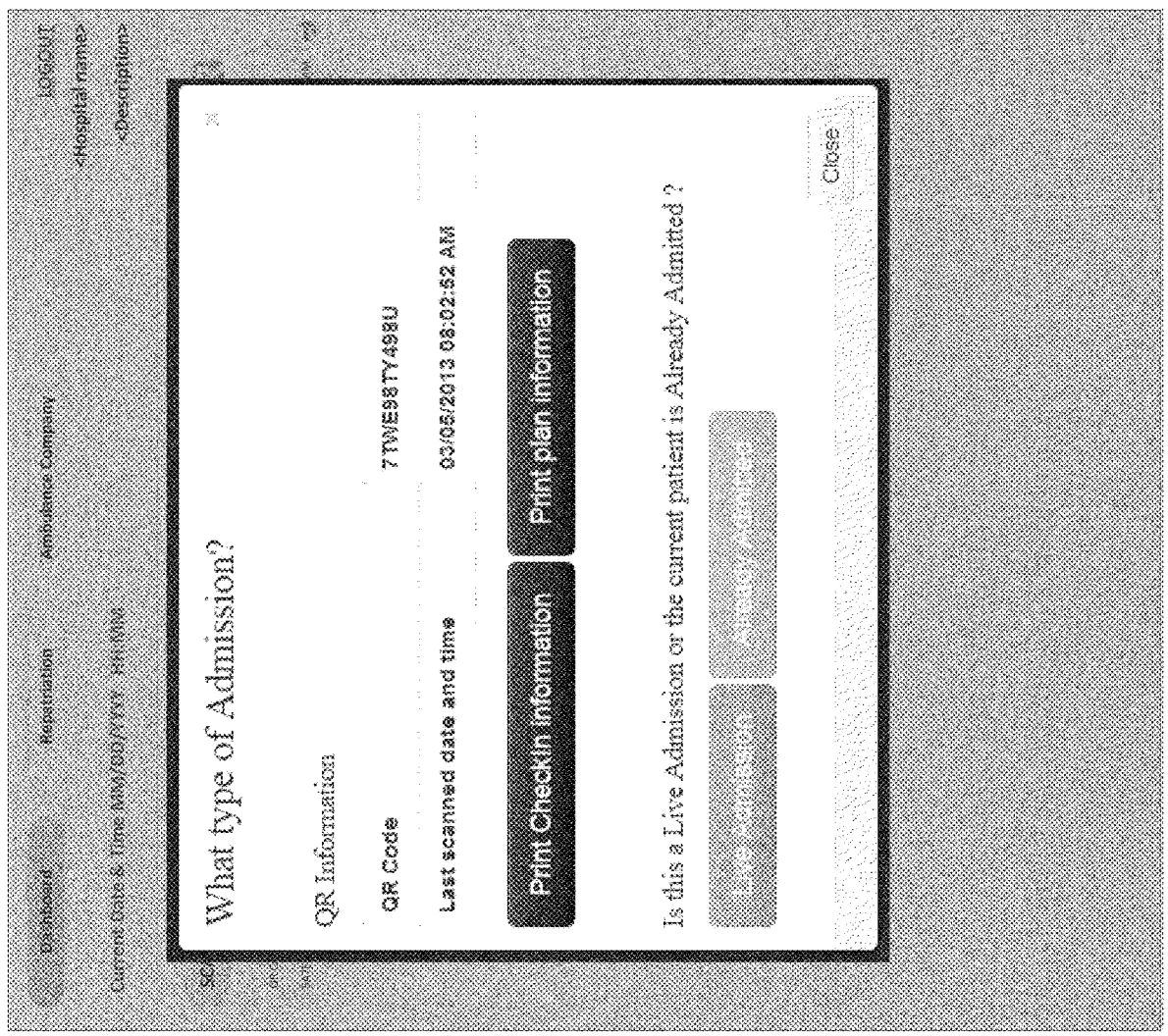
Figure 3F:
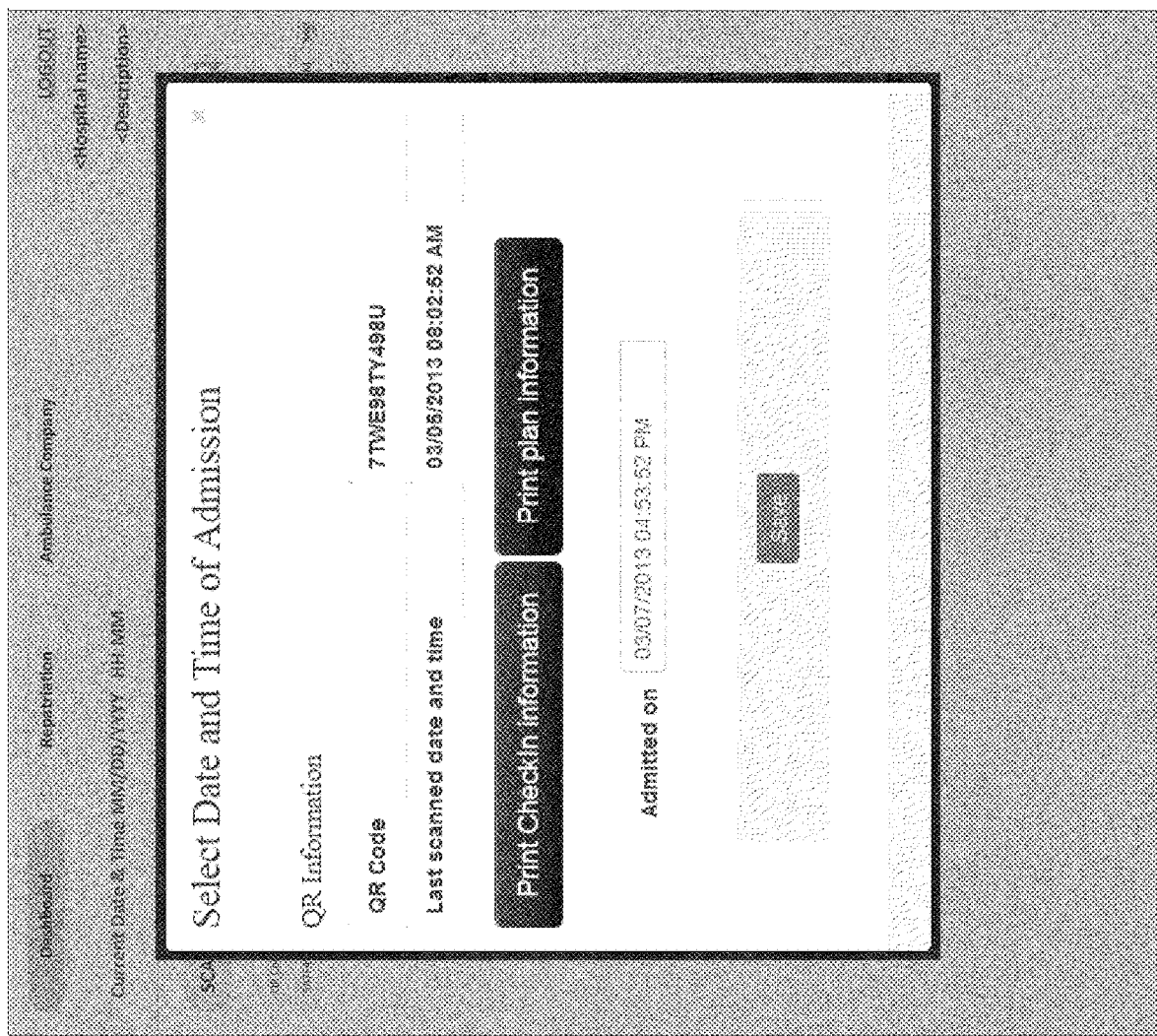
Figure 3G:
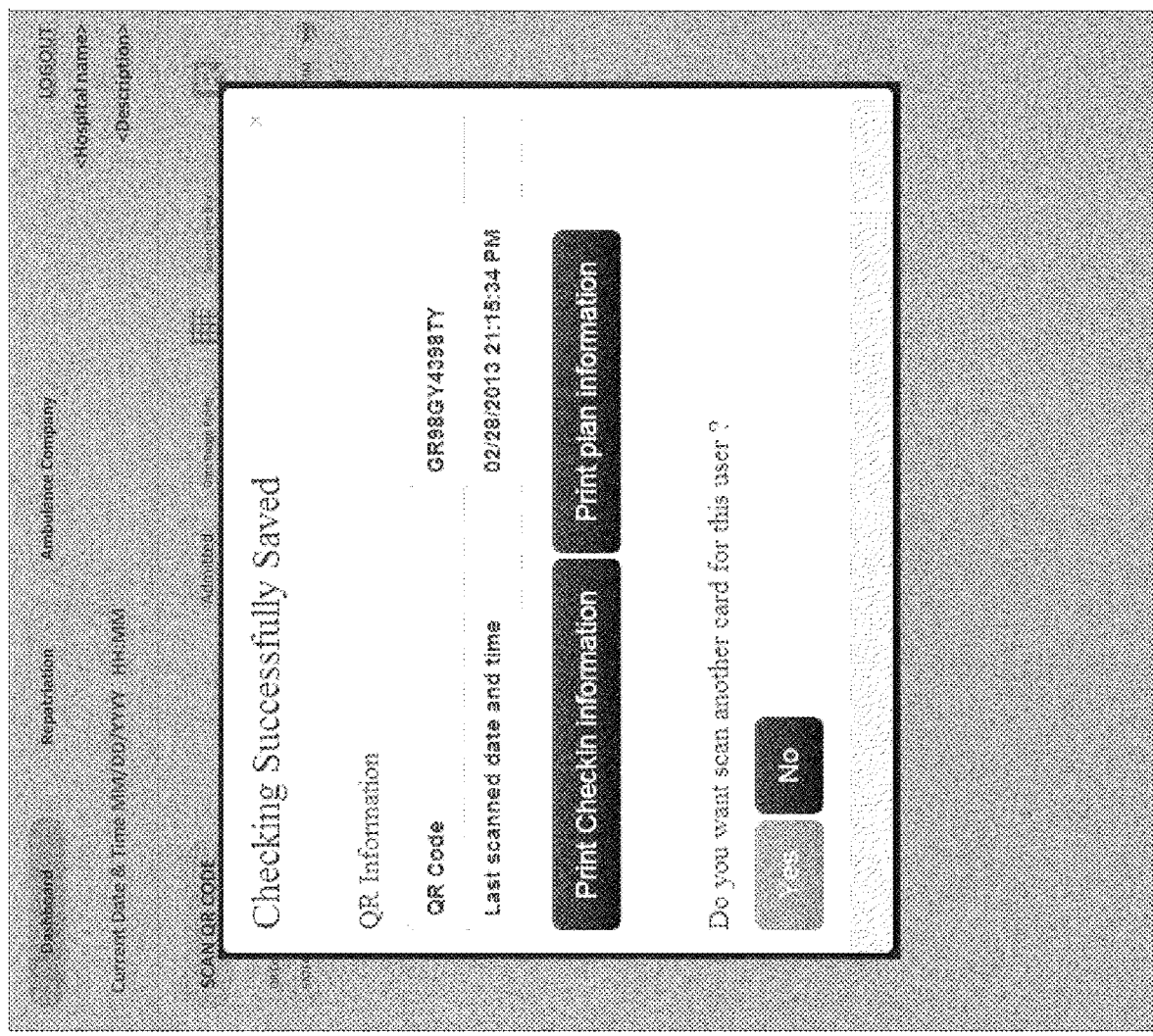

In the illustrated flow of FIG. 3A, the member's QR code is successfully scanned, and in block 306, the system displays patient information associated with the QR code, as shown in FIG. 3D. For example, the interface may display the QR code ID, member name, date of birth, last scan date and time, and a link to download the member's insurance plan. In block 308, the hospital admissions clerk selects whether the scanned QR code corresponds to entry of the member to the emergency department (ER) or the admission department. This option is illustrated with selectable radio buttons in the interface shown in FIG. 3D. In block 312, if the admission is to the ER, the hospital admissions clerk indicates whether the patient is being admitted, or only for a visit. If admission, then the system displays the interface of FIG. 3E, at which point the clerk, as shown in block 310, indicates whether the admission is "live" (i.e., the patient is being admitted at that moment) or whether the patient has already been admitted (i.e., the clerk is entering the member into the system after admission). In block 314, the clerk has selected that the member has been previously admitted, and so is provided with the opportunity via the interface shown in FIG. 3F, to enter a date of time of patient admission. The system may automatically populate this field with the current date and time, while allowing the clerk to modify if needed. If, in block 310, the admissions clerk indicates that the admission is live (or if, in block 312, the admissions clerk indicates an ER visit), the method proceeds to block 316, in which case the system uses the current date and time for admission. The result is shown in the interface of FIG. 3F. In block 318, the admission has been successfully saved, and the clerk is prompted to indicate whether the member has an additional card to be scanned, for example as shown in the interface of FIG. 3G. If the member does have another card (for example if a member has multiple insurers, she may have different cards with different QR codes associated with each), then the process begins again at block 302. If the member does not have another card, the process is completed.

Figure 4A:
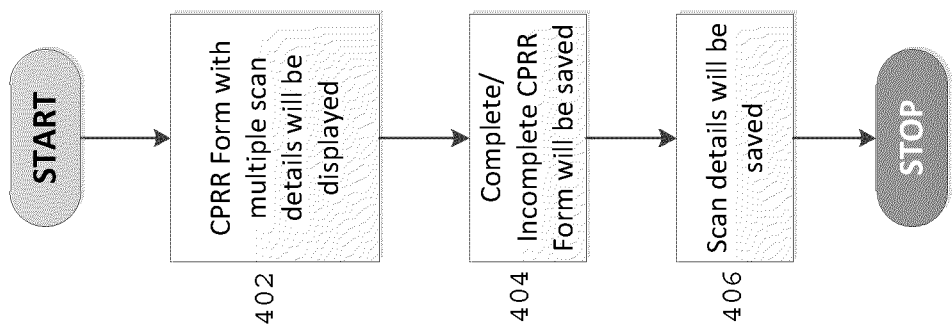
FIG. 4A illustrates an example repatriation request initiation process for repatriation management.
Figure 4B:
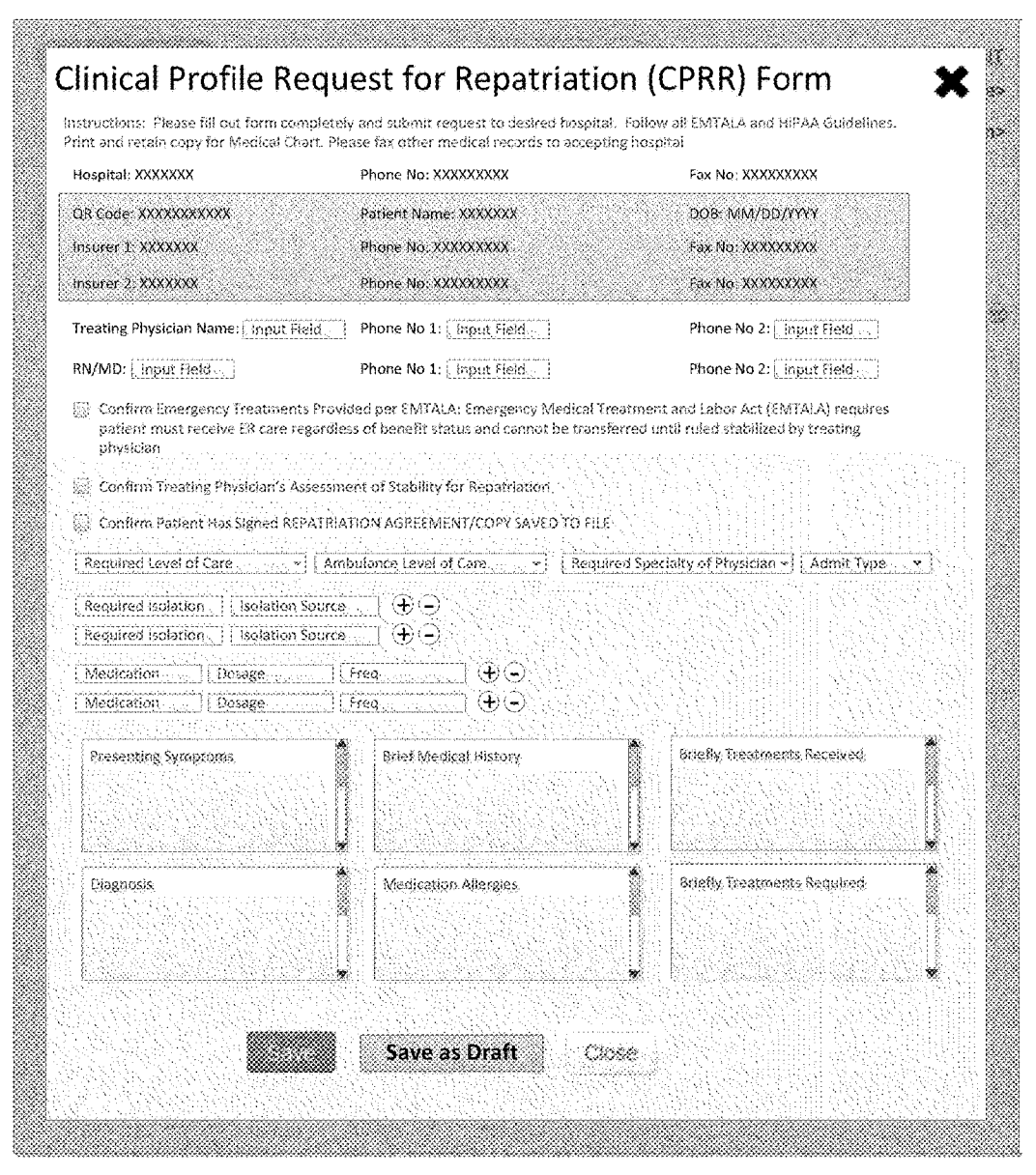

FIG. 4A illustrates an example repatriation request initiation process for repatriation management, and FIG. 4B illustrates an example user interface that may be displayed throughout the process. The process begins in block 402 with displaying the clinical profile request for repatriation (CPRR) form, for example as illustrated in FIG. 4B. In some embodiments, the CPRR form can be automatically populated with patient information based on scanning of the patient's QR code. For example, upon scanning the patient's QR code and initiating the repatriation process, the repatriation management system may automatically retrieve patient medical data, for example from electronic medical records or other sources, and populate the relevant fields of the CPRR. Hospital staff (for example a case worker assigned to the patient) may also manually complete the CPRR form to provide the relevant clinical data, for example treating physician name, required level of care, ambulance level of care, required specialty of physician, admission type, required isolation, required medications, with dosages and frequencies, any presenting symptoms, brief medical history, brief summary of treatments received, diagnosis, medication allergies, brief treatments required, etc. In various embodiments, more or fewer of these fields may be provided on the CPRR form. In block 404, the CPRR form is saved, whether in complete or incomplete status, and in block 406 the member's scan details are saved.

Figure 5A:
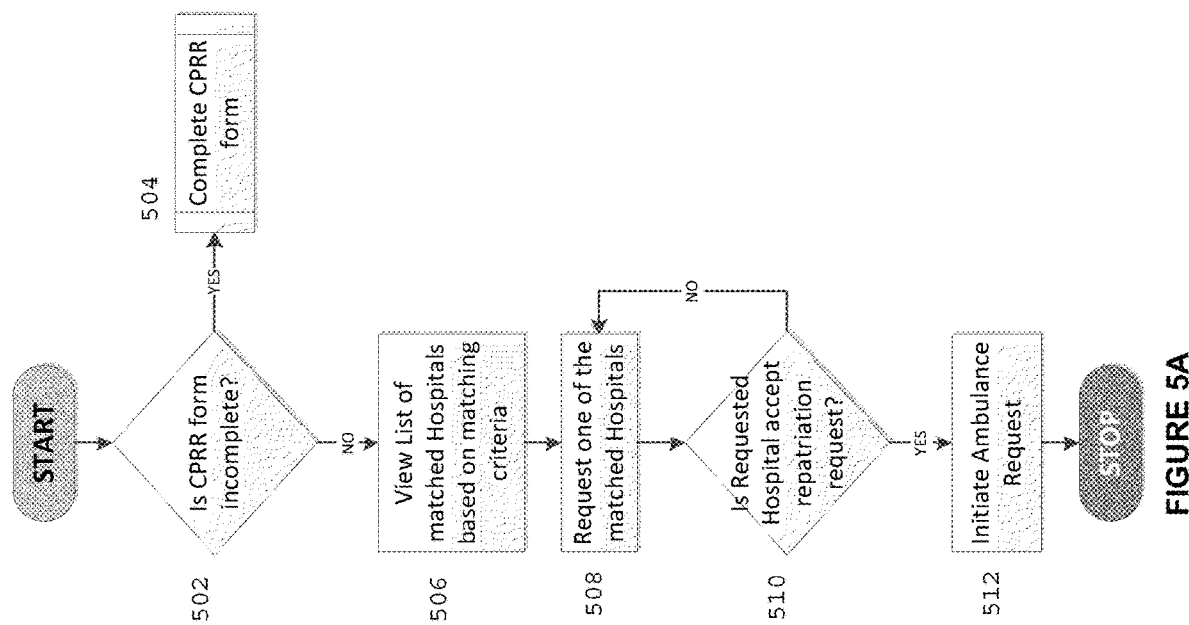
FIG. 5A illustrates an example hospital matching process for repatriation management.
Figure 5B:
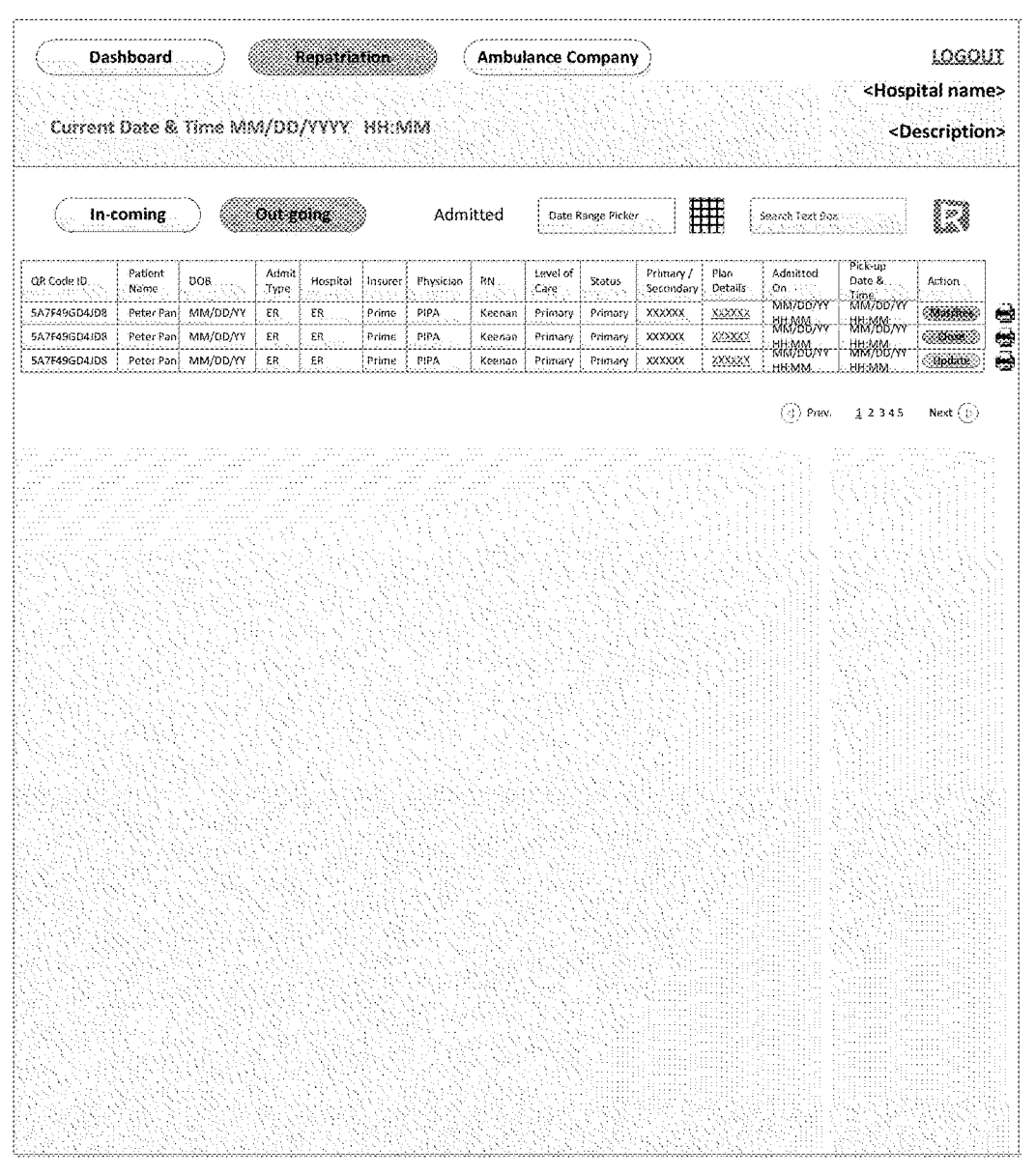
Figure 5C:
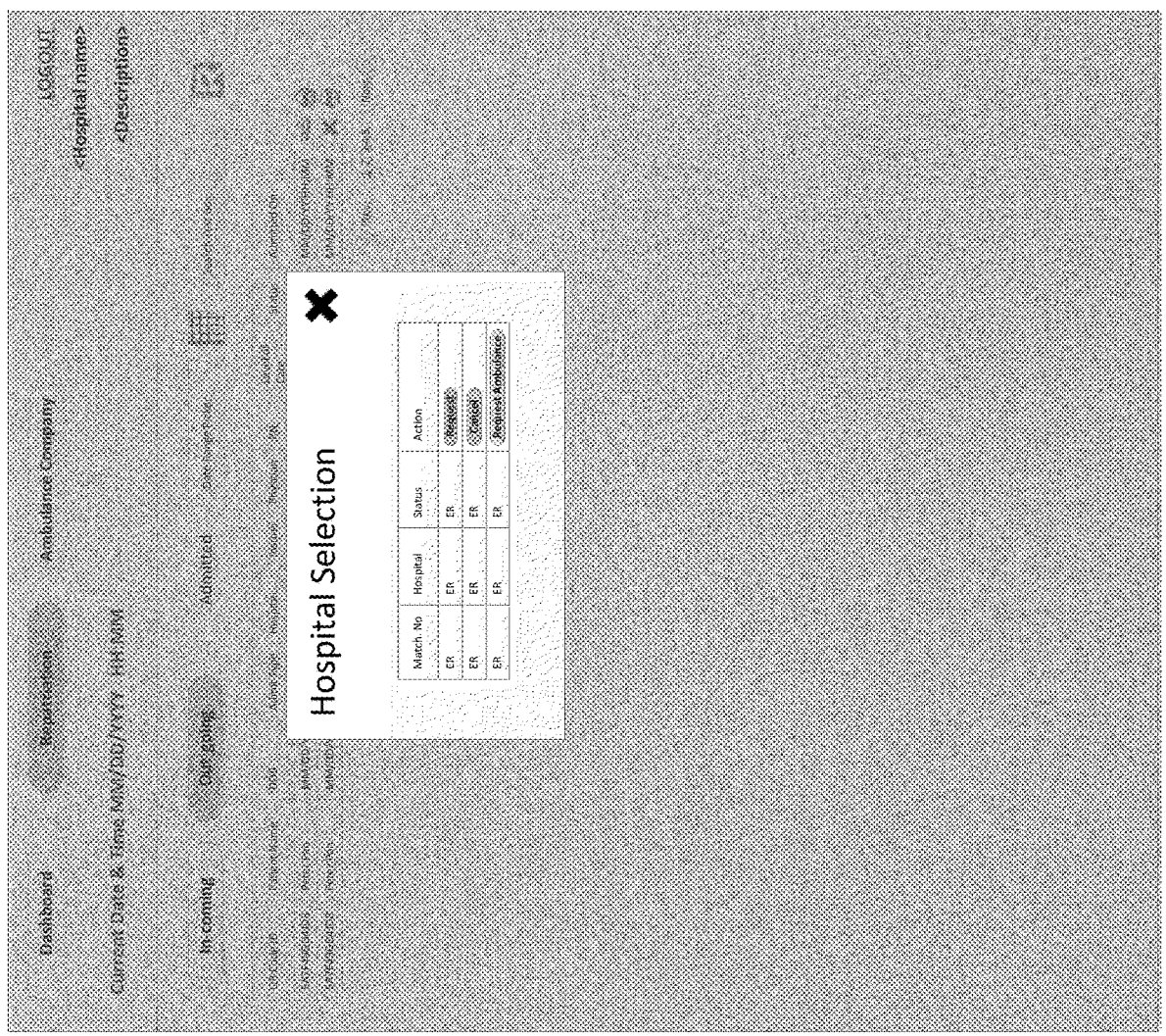

FIG. 5A illustrates an example hospital matching process for repatriation management, and FIGS. 5B-5E illustrate example user interfaces that may be displayed to different entities throughout different points in the process. The matching process begins in block 502 with querying whether the CPRR form is incomplete. If the CPRR form is not complete, then in block 504 hospital staff is prompted to complete the CPRR form, and the process cannot proceed until it has done so. Once the CPRR form is complete, the process continues in block 506 with viewing a list of matched hospitals based on matching criteria. For example, admitting hospital staff may view the interface as shown in FIG. 5B, which lists out-going repatriation requests. On the right-most column, possible actions are identified next to individual patients. By selecting the "Matches" button, a list of matched hospitals can be retrieved. The repatriation management system automatically identifies a number of matched hospitals based on the matching criteria, which can include for example insurance network, physician specialty, isolation status, etc. FIG. 5C illustrates a user interface in the form of a pop-up display that lists the matched hospitals. The first line illustrates a hospital for which repatriation has not yet been requested. The process continues in block 508 with requesting one of the matched hospitals, for example by clicking the "Request" button in the pop-up window of FIG. 5C. Once requested, the available action next to the requested hospital changes to "Cancel", which allows the admitting hospital staff to cancel the repatriation request if desired. In block 510, if the requested hospital accepts the repatriation request, then the display in FIG. 5C allows an action of "Request Ambulance", the selection of which is reflected in block 512. In the event that the requested hospital does not accept the repatriation request in block 510, then the admitting hospital is notified, and so may initiate another repatriation request to a different hospital. In some embodiments, the admitting hospital may initiate repatriation requests to multiple hospitals in parallel.

Figure 5D:
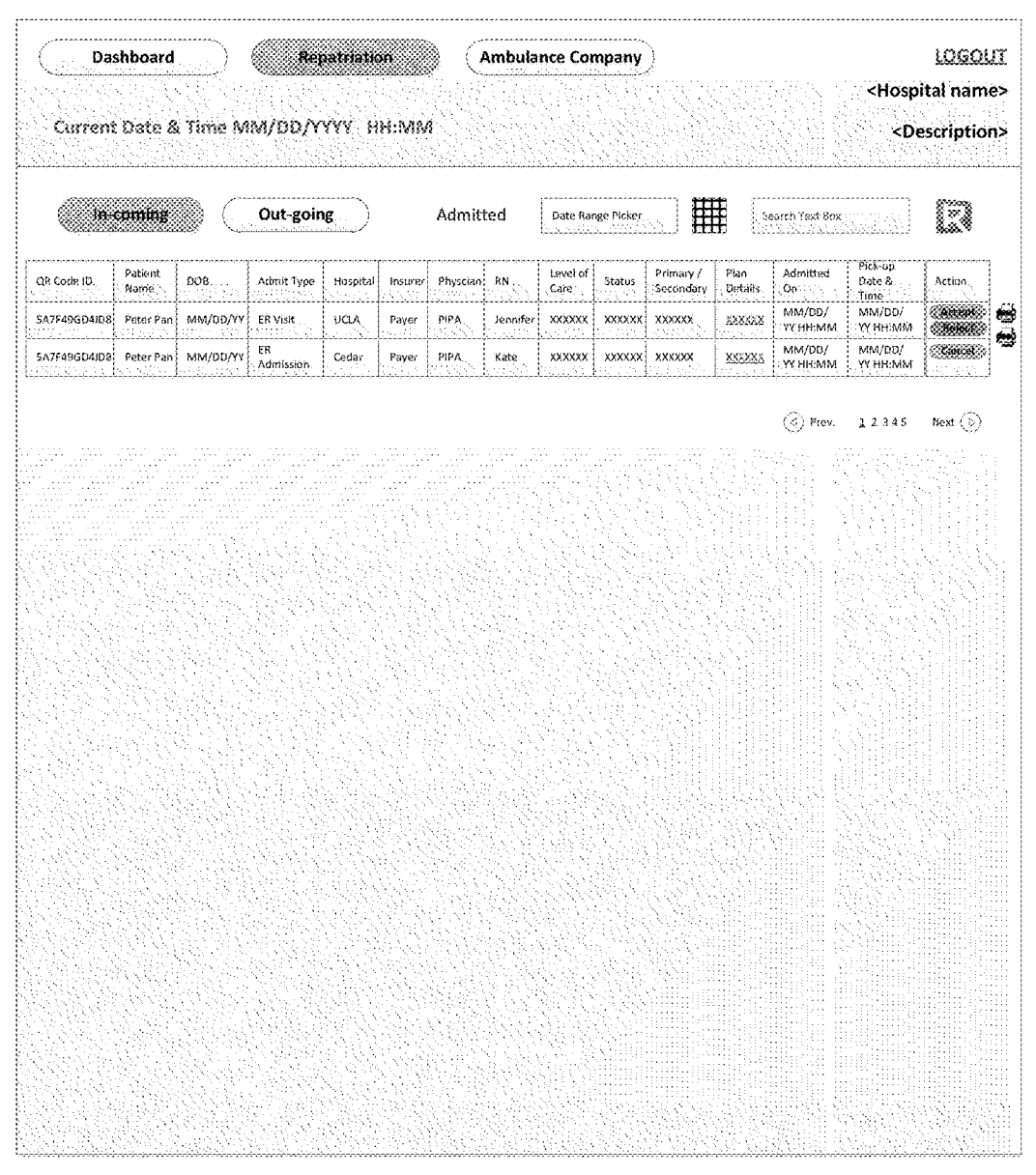

FIG. 5D illustrates an interface as shown to a destination hospital, in particular providing a list of incoming repatriation requests. In the right-most column are provided action items for various patients. For example in the first row, a new repatriation request may be acted on by the destination hospital by choosing to "Accept" or "Reject" (reflecting block 510 of the process described above). In the second row, a repatriation request has previously been accepted by the destination hospital, and the corresponding available action item allows the destination hospital to select "Cancel", for example in the event that the destination hospital is no longer able or willing to accept the incoming repatriation.

Figure 6A:
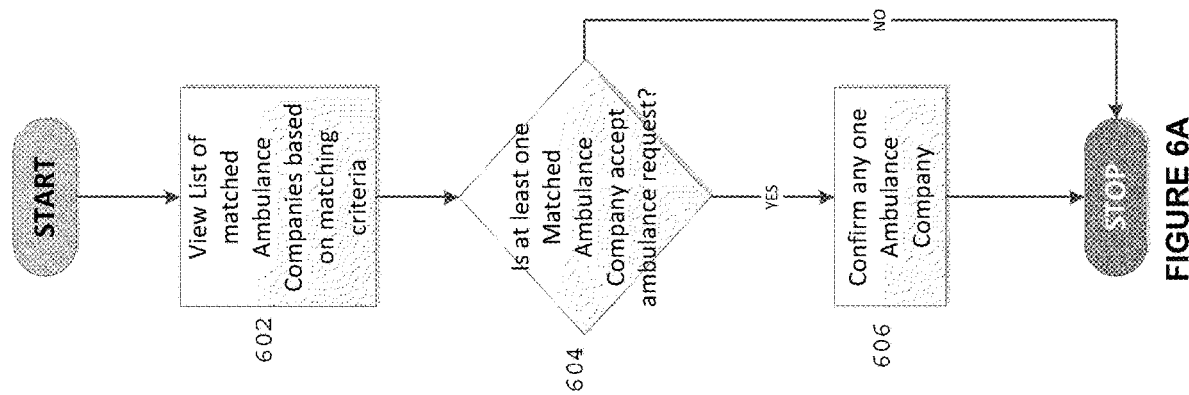
FIG. 6A illustrates an example ambulance matching process for repatriation management.
Figure 6B:
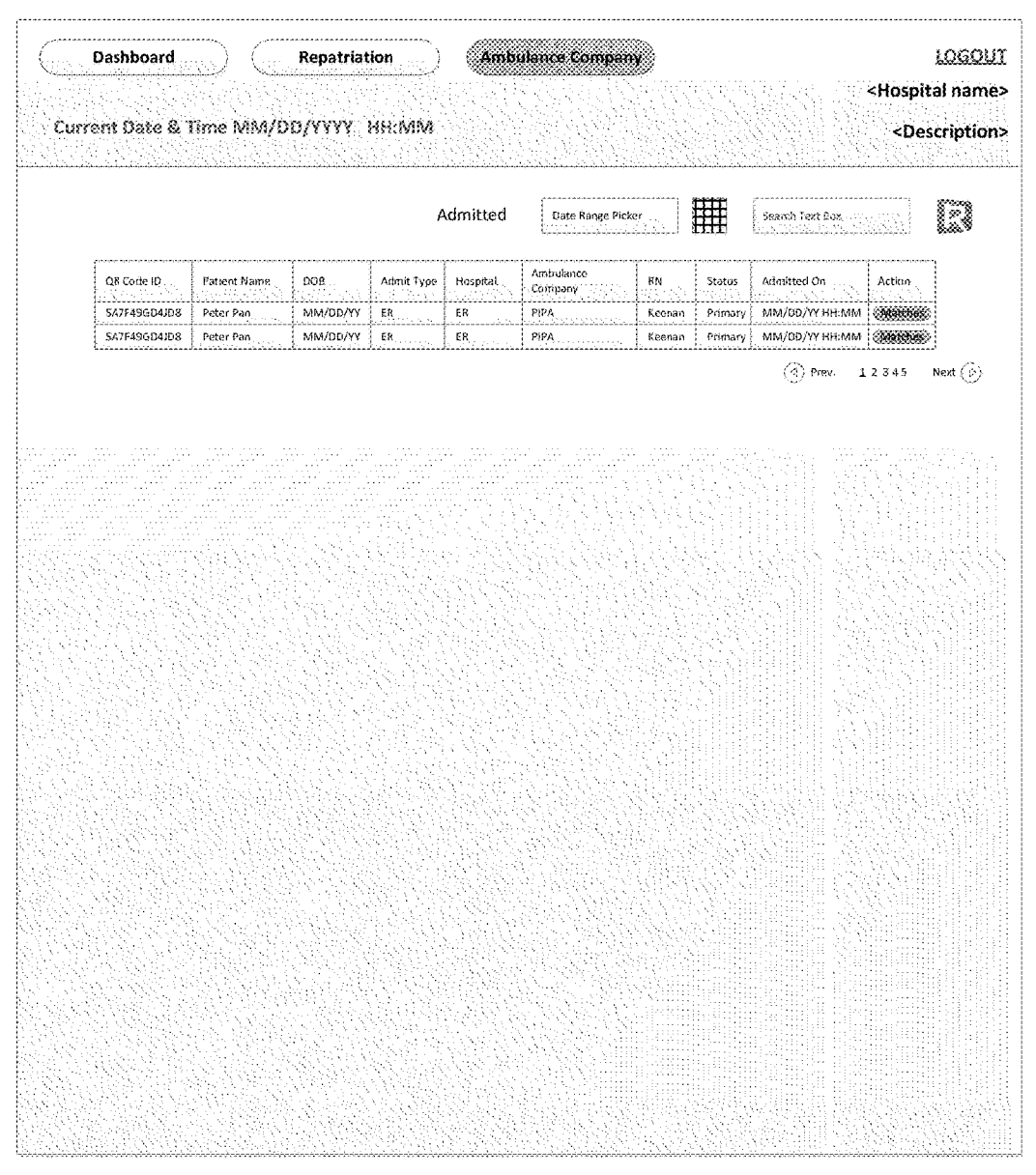
Figure 6C:
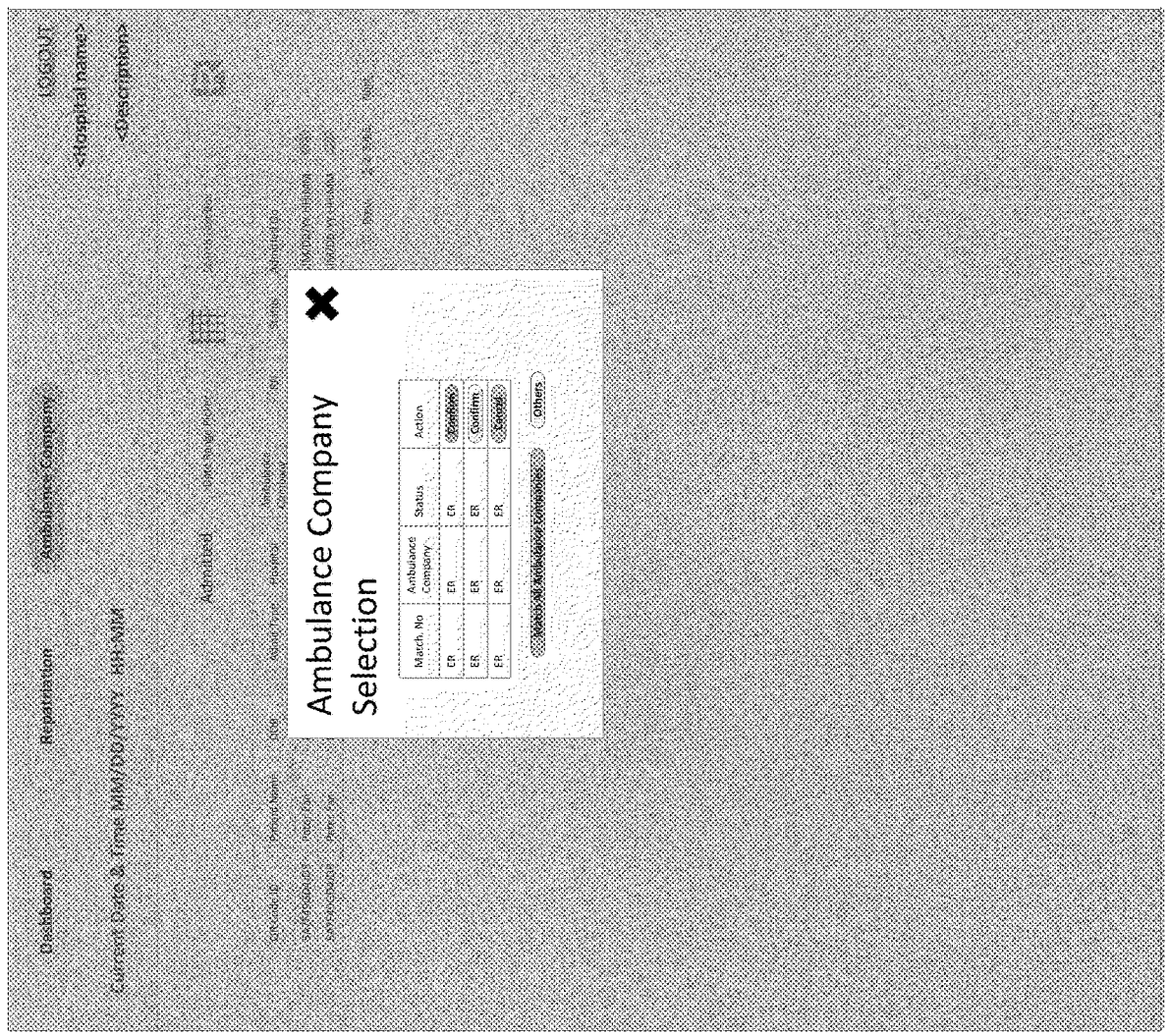

FIG. 6A illustrates an example ambulance matching process for repatriation management, and FIGS. 6B-6E illustrate example user interfaces that may be displayed to different entities throughout different points in the process. The process begins in block 602 with staff an admitting hospital viewing a list of matched ambulance companies based on matching criteria. For example, the admitting hospital may be provided with a user interface as illustrated in FIG. 6B. By selecting "Matches" from the available action in the right-most column, a list of matching ambulance companies (or other medical transport providers) can be displayed for that particular patient. A list of matching ambulance companies may be displayed in a pop-up display, for example as illustrated in FIG. 6C. The ambulance companies may be matched to the patient by a number of different criteria, for example insurance network, level of care required during transport, isolation needed, or any other clinical factors. In some embodiments, a transport request may automatically be transmitted to all matching ambulance companies. In other embodiments, admitting hospital staff may select one or more matching ambulance companies to send a request for transport of the patient from the admitting hospital to the selected destination hospital.

Figure 6D:
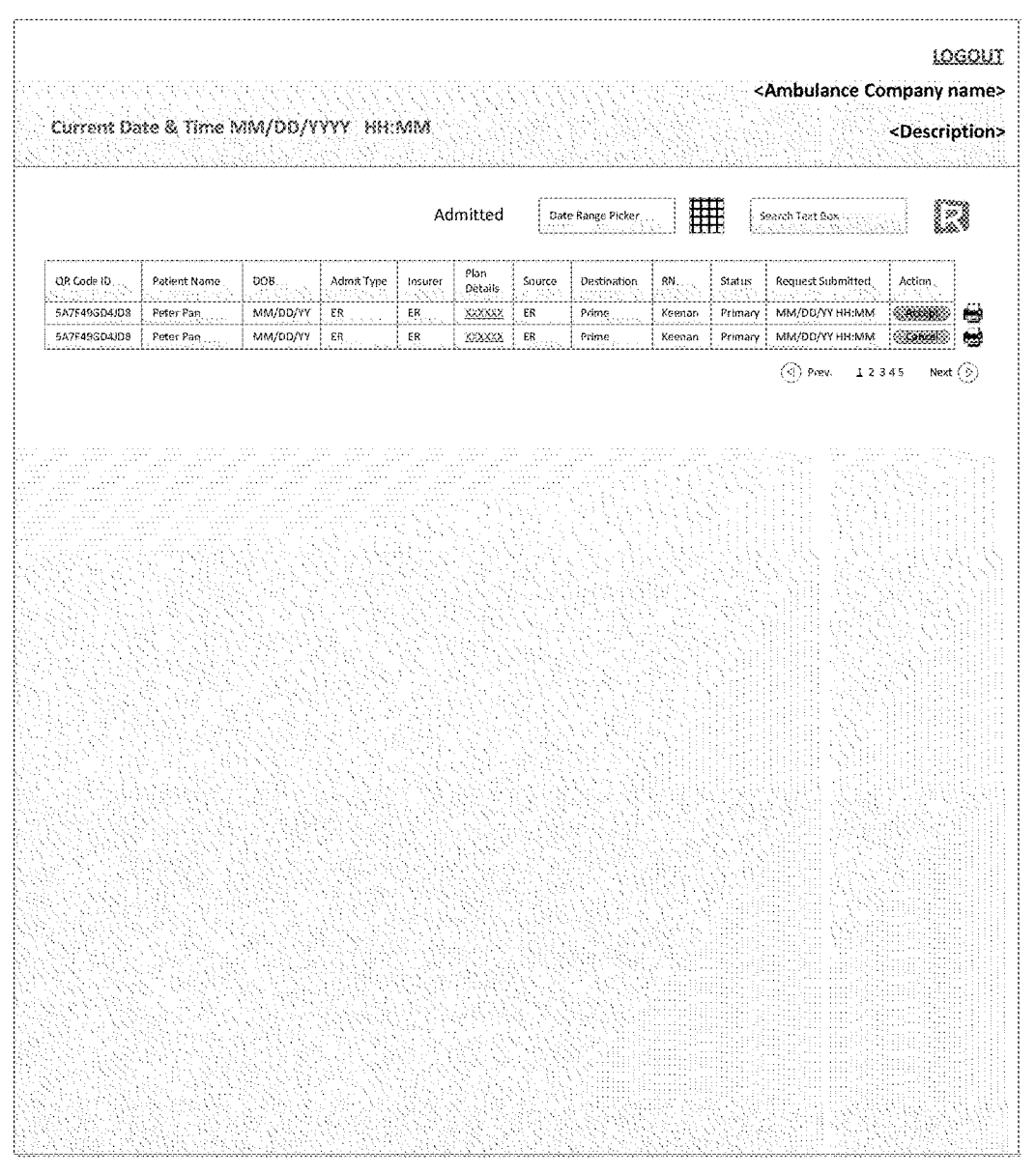
Figure 6E:
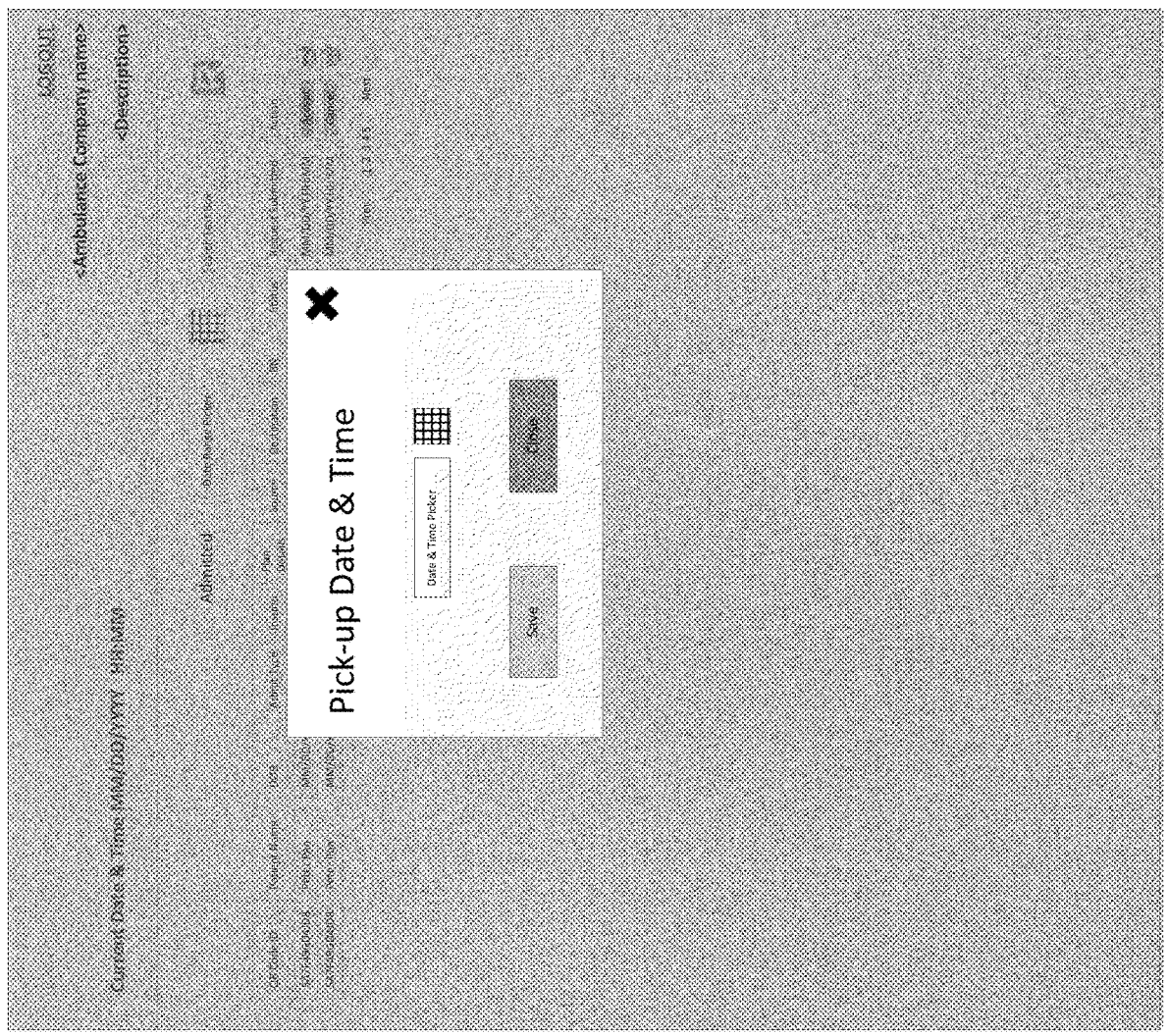

The process continues in block 604, in which matching ambulance companies are able to respond to the requests. For example, a user interface can be displayed to an ambulance provider as shown in FIG. 6D. As shown in the right-most column, an available action item for the patient in the first row is to "Accept" the request. Once the request has been accepted, the available action changes to "Cancel", allowing the ambulance provider to cancel the acceptance in the event that transport can no longer be provided for the particular patient. Upon selecting "Accept", the ambulance provider may optionally enter a specified pick-up date and time in a pop-up display as illustrated in FIG. 6E. If, in block 604, at least one matched ambulance company has accepted the ambulance request, then in block 606 the admitting hospital then confirms any one ambulance company for transport of the patient.

Figure 7:
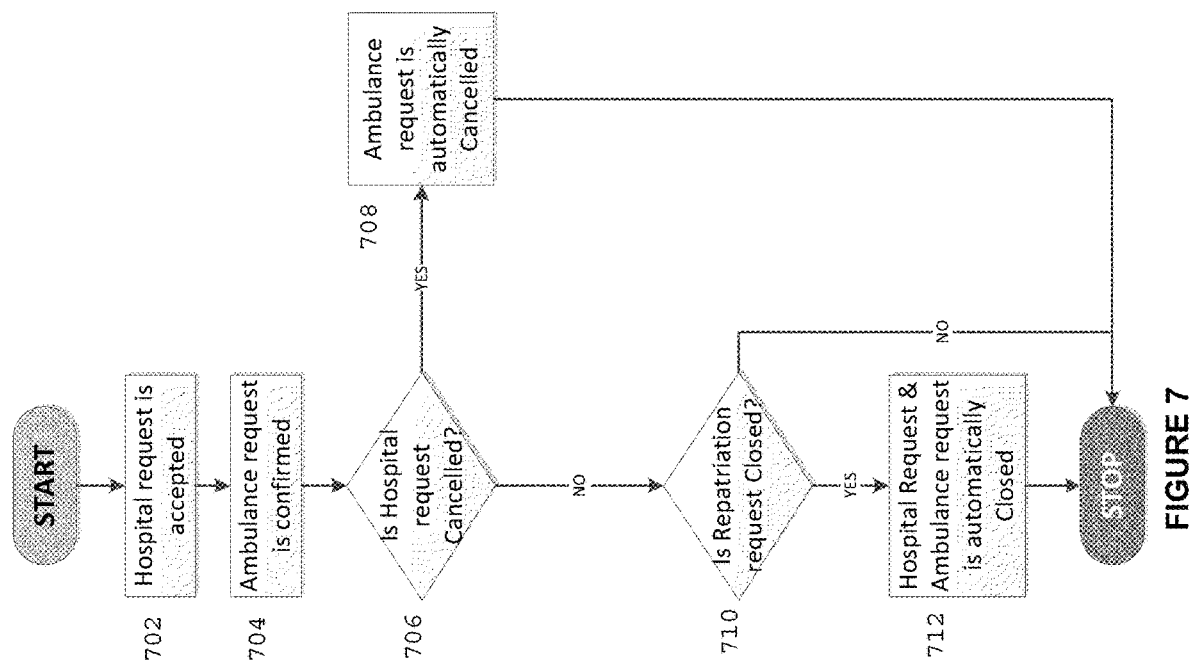
FIG. 7 illustrates an example relationship between a hospital request and an ambulance request.

FIG. 7 shows an example relationship between a hospital request and an ambulance request. These processes have been described above separately, but in use there may be multiple ambulance requests and hospital requests ongoing simultaneously. As shown in block 702), for example a hospital request may be accepted (for example via the process shown in FIG. 5A), and in block 704 an ambulance request may be accepted (for example via the process shown in FIG. 6A). In block 706, if the hospital request has been cancelled, whether by the admitting hospital (outgoing repatriation) or destination hospital (incoming repatriation), then the ambulance request is automatically cancelled in block 708 and the process is complete. If, in block 706, the hospital request has not been cancelled, then the process queries whether the repatriation request is closed. If it has been, then the hospital request and ambulance request are automatically closed in block 712. If the repatriation request has not been closed in block 710, then the process is complete.

Discharge Management System

Acute care patients who are hospitalized with a medical condition and are not medically stable typically become sufficiently medically stable to be discharged from the acute care hospital setting but may have a chronic condition and continue to require skilled nursing care. These patients typically are transferred to medical facilities that rank below an acute care hospital but include a skilled nursing staff and/or physicians on-call to tend to the patient's medical needs. These facilities can include long term facilities, other sub-acute facilities, skilled nursing facilities, and home care. An example might include a victim of a serious accident who has progressed sufficiently in the healing process to leave the acute care facility (typically a hospital) but requires further treatment including physical therapy. The hospital staff typically includes a hospital case manager who serves as a liaison between the hospital and the sub-acute facilities. Likewise, each discharge facility includes a case manager.

When a patient is scheduled to be discharged from an acute hospital setting but requires further treatment, the patient is typically transferred to one of three levels of discharge facility. The hospital case manager communicates with the case managers of a plurality of discharge facilities to identify a suitable facility to transfer the patient. For example, the discharge facility must have suitable accommodations and have the ability to treat the patient having a particular condition. Likewise, the case managers of the discharge facilities must visit the more clinically complex patient in the hospital for the purpose of evaluating the patient, reviewing the patient's records, test results and the like in order to determine if the particular discharge facility can provide the required care to the patient, and whether the patient's condition is appropriately stable, The patient at the acute care facility is evaluated regarding clinical and infectious needs, blood chemistry and other tests to generate an evaluation report. The evaluation report generated by the case manager of the sub-acute facility is utilized by the discharge facility to determine whether the patient will be accepted by the facility, consistent with the rules of the local health department. This inquiry is to determine whether a particular patient with a particular infection or condition at a particular time can be housed with other patients resident in the discharge facility without communicating the infection. This process of back-and-forth communications between multiple facilities and case managers, hospital visits, patient evaluations, and reviewing of evaluation reports by both the hospital case manager and the case managers of a plurality of sub-acute facilities is very time consuming and costly.

There is a need in the art for a system and method that facilitates the transfer of acute care hospital patients to off-site, discharge medical and other skilled nursing facilities upon the discharge of the patient from the acute care facility beyond an exchange of information and without relying on the services of case management workforce. Embodiments of the present web-based system enable bedside nursing personnel to promptly enter patient clinical information into a computerized system during shift reports, promotes communication between the acute care facility personnel and the discharge medical facility personnel regarding facility bed availabilities, affords continuous online matching of hospital patients to appropriate open beds and services, online patient/family facility education, virtual visit videos and facility preferences, information and isolation monitoring, provides secure online access to physicians and insurance company payers to patient clinical information for automatically authorizing or denying patient expenses accrued by the acute care facility for services rendered to the patient, identifies discharge issues and formulates correlating resolutions, and eliminates the need for hospital and insurance company case managers.

Figure 8:
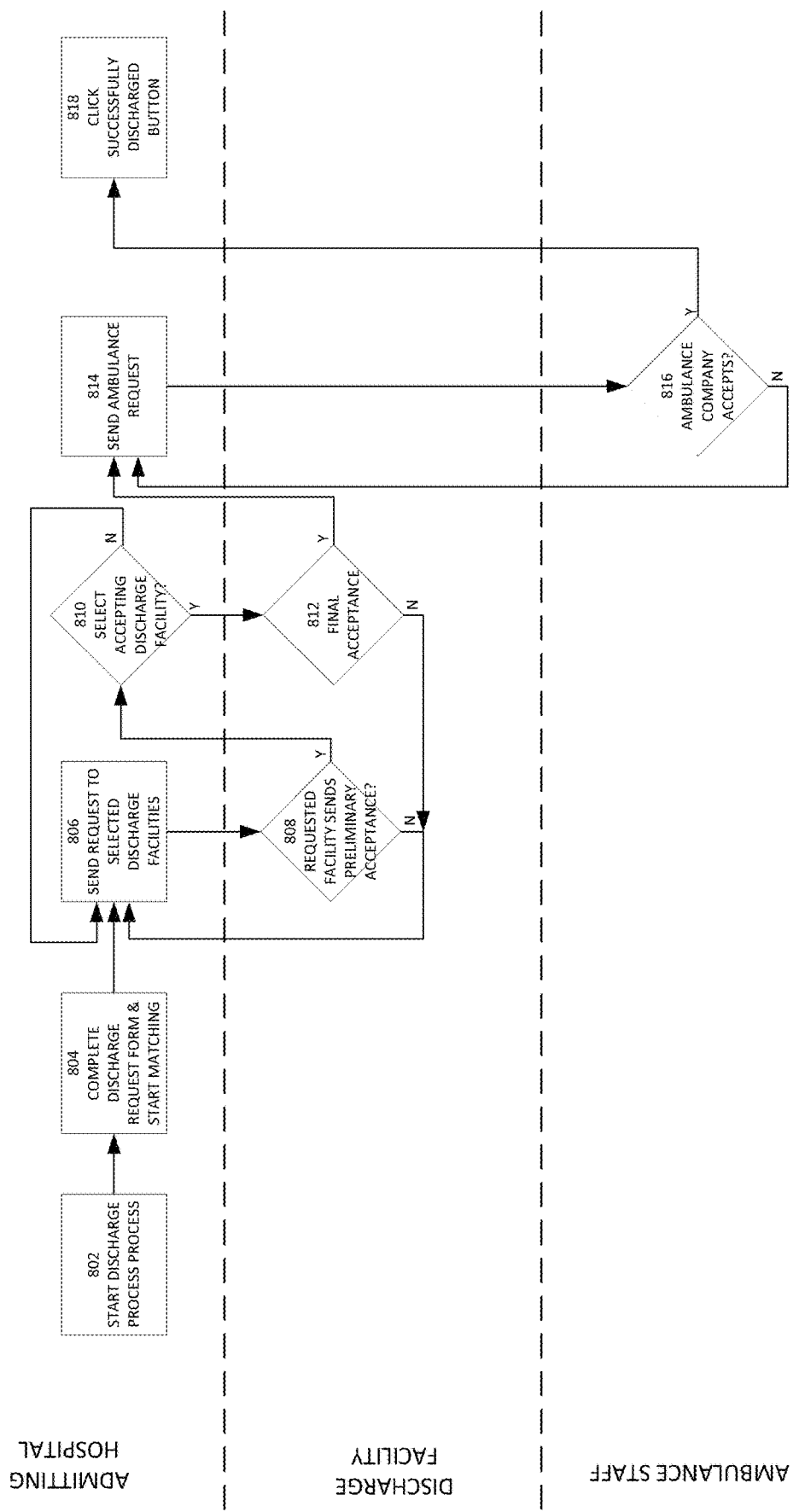
FIG. 8 illustrates an example process for discharge management.

FIG. 8 illustrates example processes for discharge management. The process flow outlines communication between three separate entities: the admitting hospital, the discharge facility, and ambulance staff. In use, this process may provide for communication between multiple entities in parallel, as described in more detail below. For example, the admitting hospital may send requests to a number of different discharge facilities, and each discharge facility may in turn receive a number of requests for a given number of beds. Likewise, ambulance staff may both receive initial requests for a number of patient transports from a variety of admitting hospitals, and the admitting hospital may send ambulance requests to any number of different ambulance companies or other medical transport providers. The process begins with the admitting hospital in which a patient, who has typically been receiving acute care, has been deemed sufficiently medically stable to begin the discharge process. Staff at the admitting hospital, for example a case manager, may begin the process in block 802 with initiating the discharge process. In block 804, a discharge request form is completed electronically, for example via a graphical user interface at a user terminal in the admitting hospital, via a mobile device carried by the hospital staff, or otherwise. The discharge request form may include relevant clinical and biographical patient data, including for example required medications, required equipment (e.g., breathing machine, dialysis, etc.), level of staff care, any need for isolation for example due to infection, etc. In some embodiments, the discharge request form may be automatically populated with patient clinical and biographical data, for example by pulling information from electronic medical records on other hospital computer systems. In some embodiments, the case manager can use a QR or barcode scanner to scan a code associated with the patient, for example a code affixed to the patient's ID card, wrist band, etc. Scanning the QR code or barcode can initiate a call to patient data previously saved in the system, which can be used to populate the discharge request form. Once the discharge request form is completed, the case manager or other admitting hospital staff can initiate matching of discharge facilities. The discharge management system analyzes the patient clinical data and the previously stored data regarding a number of discharge facilities. The system matches the patient to all discharge facilities meeting the specified criteria. For example, depending on the patient's clinical information and the required level of care, the discharge management system may compute matches to one or more discharge facilities, such as a long term care facility, a sub-acute facility, a skilled nursing facility, or to home care with a periodic visit from a medical professional.

In block 806 the case manager can send requests to selected discharge facilities. In some embodiments, a list of matching discharge facilities computed by the discharge management system can be displayed to the case manager, for example via a graphical user interface on a computer terminal or mobile device. The case manager can select from among the listed discharge facilities and choose to send requests to one or more. In some embodiments, the case manager may initiate requests to several different discharge facilities in parallel. This allows the case manager the confidence that, should her first choice discharge facility be unable or unwilling to accept the discharge request, other discharge facilities may provide acceptance so that appropriate patient discharge can be facilitated, without having to begin the entire process entirely.

Block 808 illustrates action on behalf of one of the selected discharge facilities. As noted above, in some embodiments a number of different discharge facilities can each receive requests in parallel for discharge of the same patient. The description herein relates to the actions and interactions for a single discharge facility, but it will be understood that in use the process can happen in parallel across many discharge facilities. In block 808, the discharge facility receives a request for discharge of a particular patient. The request can be received, for example, via a graphical user interface accessed on a computer terminal or mobile device. In some embodiments, the graphical user interface is provided via a network connection to the patient discharge management system, for example via a web portal that is separately accessible by the separate entities. By securely logging into such a web portal, each entity may be provided with a different set of graphical user interfaces as needed. For example, in block 808, the discharge facility may see a list of incoming discharge requests. By selecting one of the requests, the discharge facility staff may access additional information regarding the patient, for example insurance information, medical condition, required medication, and so forth. The discharge facility has the option of either sending a "preliminary acceptance", if they have determined that they are at least interested in accepting the patient. The discharge facility may conversely determine that they do not wish to accept the patient, for example due to space restrictions, concerns over insurance, medical condition, or otherwise. Should the discharge facility decline the request, the admitting hospital staff will be notified, for example via the web portal, and the admitting hospital may initiate additional discharge requests as needed. In some embodiments, the admitting hospital will have previously submitted to multiple discharge facilities, and so upon receiving a notification that one of the discharge facilities has declined, the admitting hospital will simply look to other discharge facilities to which it has transmitted requests. Should the discharge facility send a preliminary acceptance, the admitting hospital will be notified, for example via the web portal.

In block 810, the admitting hospital may select or decline the discharge facility from which it has received a preliminary acceptance. For example, an admitting hospital might send out requests to five discharge facilities and receive two preliminary acceptances. From among those, the admitting hospital might select a single discharge facility. At that time, as shown in block 812, the discharge facility can be notified of the selection by the admitting hospital, and may then choose whether to transmit a final acceptance. Should the discharge facility choose not to accept at this stage, the admitting hospital will be notified and will continue to review the status of requests to other discharge facilities. Should the discharge facility elect to communicate a final acceptance of the patient, the admitting hospital will be notified, for example via a user interface on the web portal.

In block 814, a request for medical transport, such as an ambulance, is sent by the admitting hospital. In some embodiments, the admitting hospital staff may view confirmation of final acceptance from the discharge facility, for example via a web portal, and may click a button or otherwise initiate the ambulance request. In some embodiments, a list of possible ambulances or other medical transport provides can be displayed to the admitting hospital staff, and one or more of those ambulances can be selected for transmission of a transport request. In some embodiments, the discharge management system may automatically communicate the transport request to all identified ambulances or medical transport providers. In some embodiments, the system may limit those ambulance providers to whom the request is sent based on a number of different criteria. For example, the system may limit the ambulance providers based on insurance status (e.g., only request ambulance providers associated with the patient's insurer), medical condition (e.g., only request ambulance providers with adequate capability to transport the patient given the medical condition), or other factor.

In block 816, action on behalf of one of the ambulance providers is illustrated. As noted above, in some embodiments a number of different ambulance providers can each receive requests in parallel for transport of the same patient. The description herein relates to the actions and interactions for a single ambulance provider facility, but it will be understood that in use the process can happen in parallel across many ambulance providers. In block 816, the ambulance provider receives a request for transport of a particular patient from the admitting hospital to the selected discharge facility. The request can be received, for example, via a graphical user interface accessed on a computer terminal or mobile device. In some embodiments, the graphical user interface is provided via a network connection to the patient discharge management system, for example via a web portal that is separately accessible by the separate entities. By securely logging into such a web portal, each entity may be provided with a different set of graphical user interfaces as needed. For example, in block 816, the ambulance provider may see a list of incoming transport requests. By selecting one of the requests, the ambulance provider staff may access additional information regarding the patient, for example insurance information, medical condition, required medication, and so forth. The ambulance provider then has the option of either accepting or declining the request. Should the ambulance provider decline the request, the admitting hospital staff will be notified, for example via the web portal, and the admitting hospital may initiate additional transport requests as needed. In some embodiments, the admitting hospital will have previously submitted to multiple ambulance providers, and so upon receiving a notification that one of the ambulance providers has declined, the admitting hospital will simply look to other ambulance providers to which it has transmitted requests. Should the ambulance provider send an acceptance, or "bid" on the transport request, the admitting hospital will be notified, for example via the web portal.

In some embodiments, the admitting hospital may receive acceptances or bids from a number of different ambulance providers, in which case an additional step of selecting from among the accepting ambulance providers may be undertaken by the admitting hospital. In such embodiments, upon selecting of the final ambulance provider for transport, the non-winning bidders (i.e., ambulance providers who accepted the request, but were not selected for final transport by the admitting hospital) will be notified automatically, for example via the web portal. Finally, in block 818, once the patient has been picked up by ambulance staff, the admitting hospital may select a "successfully discharged" button or otherwise indicate that discharge has been completed. The discharge management system may automatically provide this indication to any number of other entities, for example the patient's insurer, non-selected discharge facilities, non-selected ambulance providers, and other staff at the admitting hospital.

The computer program resident within the discharge management system 103 may analyze clinical patient entered data into the system, as well as the condition of the patient for abnormal readings, discharge/placement issues (restraints/agitation), feeding tubes placed through the nose, medications, etc. An example of first tier data analysis by the computer program includes comparison with normal range stored data in the system data storage memory. Measured parameters include, for example, body temperature, blood pressure, heart rate, respiration rate, laboratory and culture results. The issue is to determine whether the measured patient data is outside of the normal acceptable range of readings. The second tier data analysis can be based upon the patient's particular history and may determine whether the patient data is a deviation from the patient's normal baseline reading for that condition. For example, suppose a normal blood pressure reading for the patient is 180/90 but the current reading is 98/48. This current reading is a significant deviation from the patient's normal states even though the 98/48 reading is within the generally accepted normal range. Consequently, this reading may not be normal for this particular patient. The third tier of data analysis can be directed to identifying discharge/placement related issues such as, for example, patient restraints since most remote care facilities may not admit a patient who is restrained. A fourth level of analysis can be directed to the appropriateness of the patient discharge from the acute care hospital with a view to risk management. The issue is whether it is appropriate to discharge a patient in view of her current condition. The fifth tier of data analysis involves analysis and resolutions regarding the impatient discharge criteria. The general inquiry is if the patient is ready for discharge, at what level should the patient be discharged to one of the remote care facilities. Should the patient in her present condition be discharged to a long term care facility, a sub-acute facility, a skilled nursing facility, or to home care with a periodic visit from a medical professional.

As a result of the analysis of the entered data, abnormal readings are noted thus identifying patient medical and hospital placement discharge problems or issues. The abnormal readings or results can include temperature, blood pressure, heart rate, respiratory rate and laboratory and culture results, active gastrointestinal bleeding, multiple inter-venous tube issues, and acute neurological problems. These patient medical and hospital discharge issues can be flagged in the patient's medical reports generated by the system so that the medical staff can be alerted to the existence these conditions. Finally, resolutions to these problems related to the abnormal medical patient and discharge related issues are formulated by the computer program for implementation by the hospital medical staff so that the patient can be discharged according to schedule.

The discharge issues specific to the pre-determined discharge "level" of the patient, that is, long term care, sub-acute, skilled nursing, or to home care, and correlating resolutions thereto will be formulated by the case management system 100. These discharge issues will periodically change and/or be updated daily by the addition of further clinical information collected and recorded in the data entry terminals by the bedside nurse. These discharge issues and corresponding resolutions may be accessed online by the bedside nurse, physician, the discharge department of the acute care hospital, managed care providers/insurance companies, discharge remote care facilities, or any other authorized party having an assigned password for use in accessing the system data storage memory.

An example of a computer program generated formulated resolution involves a patient that is agitated and/or subject to restraints. The staff nurse enters data into the data entry terminals noting that the patient is agitated and/or restrained. The monitor screen sets forth and enumerates possible solutions determined by the computer program resident within the system server. The computer program generated report may suggest considering sedatives or anti-anxiety medications if the patient is agitated. If the patient is restrained, the proposed resolution may be to sedate the patient plus the use of mittens or so called "freedom splints" (which permit some movement by the patient but restrain such that the patient cannot remove an inter-venous needle) when deemed safe for use. As it relates to the consideration of patient discharge criteria, a sub-acute care facility may not admit a discharged patient if the patient is agitated or restrained. However, it may be acceptable for an acute long term care facility to admit a mildly agitated or restrained discharged patient. Therefore, the computer program resident within the system server will monitor this problem and alert medical personnel at the acute care hospital to proposed solutions to the restraint discharge issue. This action may be necessary to eventually remove the patient from restraints so that a sub-acute care facility will accept the patient upon discharge from the acute care hospital.

Another example of a computer program generated formulated resolution involves a patient that has a nasogastric tube (i.e., temporary feeding tube) inserted into her nose and fished downward into the stomach. A sub-acute care facility may be unable to accept a patient fitted with a nasogastric tube. The computer program within the system server will identify each of the patient discharge issues and conditions and alert the medical personnel as to this problem and provide potential resolutions therefore. After a fixed period of time, the computer program will provide the medical personnel with these resolutions by entering comments on the website associated with the system server. The website can be accessed by a medical personnel monitor (not shown) assigned to track the progress of a certain number of patients. For example, the case management system 100 will recognize that a patient has been on an inter-venous tube for too many days, or that the nasogastric tube placed through the patient's nose (used for short term feeding) should be replaced with a percutaneous endogastric tube (PEG) which can be inserted into the patient's stomach for longer term feeding of the patient. The case management system 100 can be programmed to address each of these patient discharge problems. These proposed formulated resolutions are stored on the system server 110 and are printed out from the system server 110 on the Daily Nursing Report and the Daily Case Management Report. Hospital personnel staff with a suitable password can access the system server 110 to review and implement the formulated resolutions.

Figure 9A:
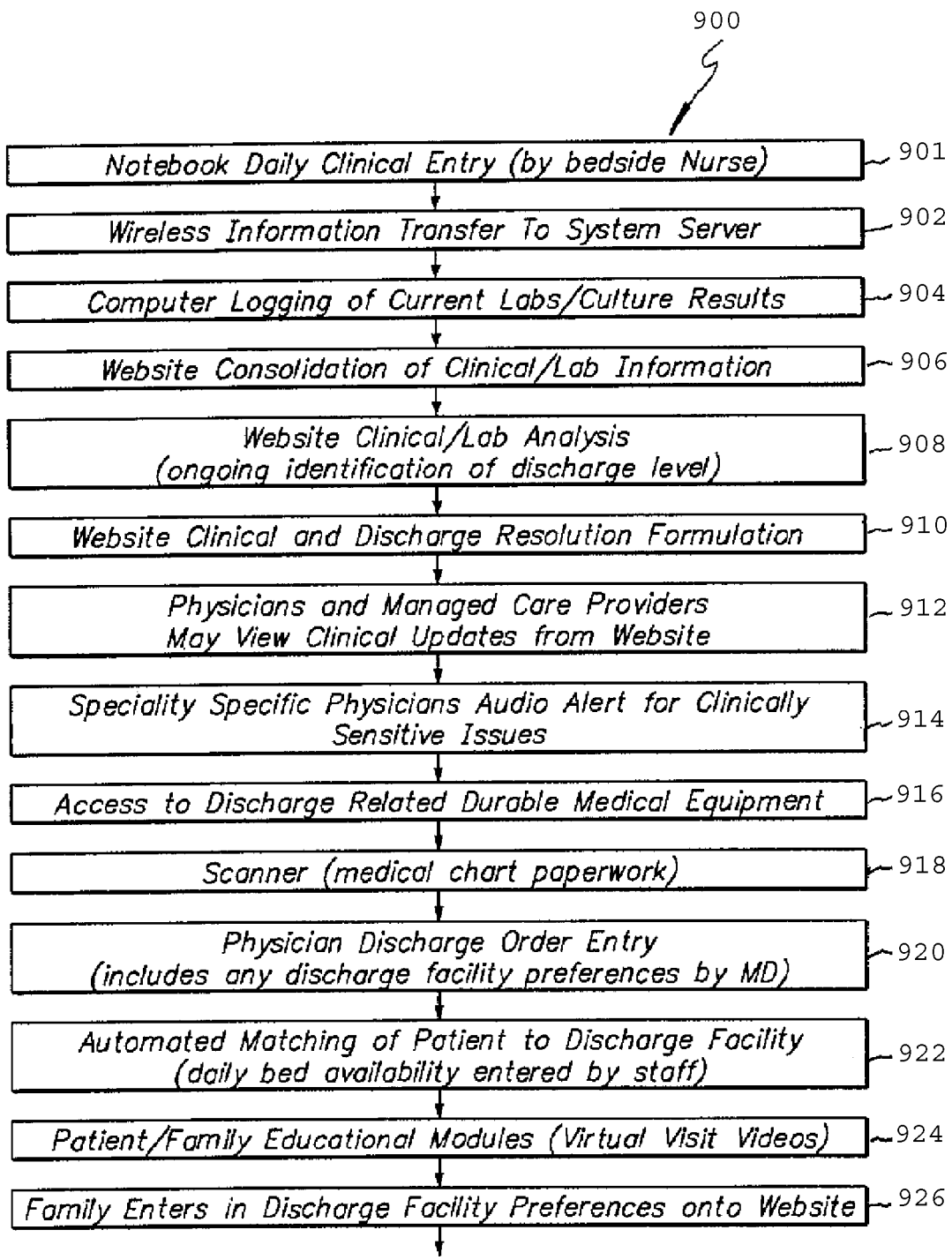
FIGS. 9A-9B illustrate an example discharge management process, from entry of clinical data to online patient/family satisfaction surveys.

The discharge management process practiced by the case management system 100 will now be discussed with reference to FIGS. 9A, 9B, 10 and 11. Referring in particular to FIG. 9A, there is shown a flow diagram 900 of the case management system 100 of FIG. 1 showing the generalized steps in a method disclosed herein. The beginning block 901 illustrates the daily entry of patient clinical data into the portable data entry terminals which can be notebook computers. The daily entries typically occur in the morning when the bedside nurse makes her rounds from patient-to-patient checking blood pressures, body temperatures and the like. The entered data can be then wirelessly transferred in block 902 as is known in the art from the data entry terminals to the system server. Simultaneously, the laboratory personnel of the acute care hospital record or log the most current patient laboratory and culture test results into the system data storage memory via one of the hospital computers as shown in block 904 in FIG. 2A. Then, the patient clinical data collected by the bedside nurse and the current laboratory results are consolidated in the system data storage memory and made accessible on the system website via the system web server in block 906, Thereafter, the computer program resident within the system server proceeds with the analysis of the clinical data and current laboratory information in block 908. The results of this analysis will guide the medical personnel in determining the ultimate "level" at which the patient will be discharged at, i.e., will the patient be transferred to an acute care long term facility or to a facility providing a lower level of care.

During the analysis of the clinical data and the laboratory test results, discharge issues and problems are identified which might prevent the patient from being discharged according to schedule. In block 910 shown in FIG. 9A, the computer program resident within the system server formulates resolutions to the patient discharge issues and problems discovered during the analysis. All of the information including the daily clinical data, current laboratory and culture results, analysis data and formulated resolutions can be stored in the system data storage memory 962. As a result, the physicians and the managed care providers or insurance companies can access and view the updated clinical information from the system website via the system web server as is illustrated in block 912. If a clinically sensitive issue exists, the case system includes the "specialty specific" physicians audio alert for clinically sensitive issues. This feature can be realized by the Automated Physicians Assistant that automatically instructs the system server to transmit a signal across the network to a mobile communications device carried by the physician for indicating when a threshold condition has occurred and corresponding data has been entered into the system data storage memory for clinically sensitive cases as indicated by block 914. The case management system recognizes that the threshold condition precedent has occurred and automatically notifies the physician. For example, as soon as a laboratory culture result for the patient is determined, the data can be entered into the system data storage memory of the system server by, for example, laboratory personnel. If the laboratory result matches or exceeds the threshold value and the threshold value of that parameter is listed on the physicians "general menu" or "personalized menu", the system server can be programmed to automatically send a signal to the mobile communications device carried by the physician. The signal can be audible or text messaging and advises the physician to check his e-mail, voice mail, system instant text messaging, or to contact the staff nurse or laboratory tech. The signal can be specifically directed to one or more physicians practicing in a relevant medical specialty.

After the clinically sensitive issues have been addressed and the patient is completing and making progress in a treatment program, a discharge schedule can be devised. The progress of the patient in the treatment program along with the analysis of the daily clinical data and laboratory results will determine what "level" of remote care facility the patient will be discharged to. That "level" of care required by the patient once she leaves the acute care hospital will determine what durable medical equipment, i.e., special equipment and resolutions to bariatric, wound vac, wound treatments, isolation equipment, and alternative safety devices the patient will need. This feature is illustrated in block 916 which indicates that the patient has access to discharge related durable medical equipment which is available from the hospital discharge department. Thereafter, block 918 indicates that the patient's medical chart paperwork can be scanned into the case management system for matching with an appropriate remote care facility. At the end of the treatment program, a "discharge order" by the physician can be entered into the patient's medical record as is indicated by block 920. This "discharge order" can include any discharge facility preference of the physician, i.e., a preference to a particular remote care facility consistent with the "level" of care required.

Along with all the data related to the patient's clinical data and laboratory results, data related to the plurality of remote care facilities, their capabilities, treatment limitations, medical staff, licensing limitations, and current bed availability data can also be entered into the system data storage memory. With this information entered into the case management system along with the "level" of care data required by the patient, the patient can be automatically matched to a list of suitable discharge remote care facilities by the computer program resident in the system server as is indicated in block 922, At this point, the patient and/or her family can be provided access to educational modules (not shown) also known as virtual visit videos as is indicated by block 924 shown in FIG. 9A. The Patient/Family Educational Modules and Videos and compact disks will be available for discharge support and are utilized to explain the discharge process and the discharge facility's services, and to answer frequently asked questions. The virtual visit video tapes and compact disks will be available for viewing, for example, in the library of the acute care hospital. The patient or a family member can obtain a password for accessing the virtual visit videos in the system server over the network. Once the patient and family have had access to the Patient/Family Educational Modules and Videos, they can enter their preferences regarding the remote care facilities on the system website via the system web server as indicated by block 926 in FIG. 9A.

Figure 9B:
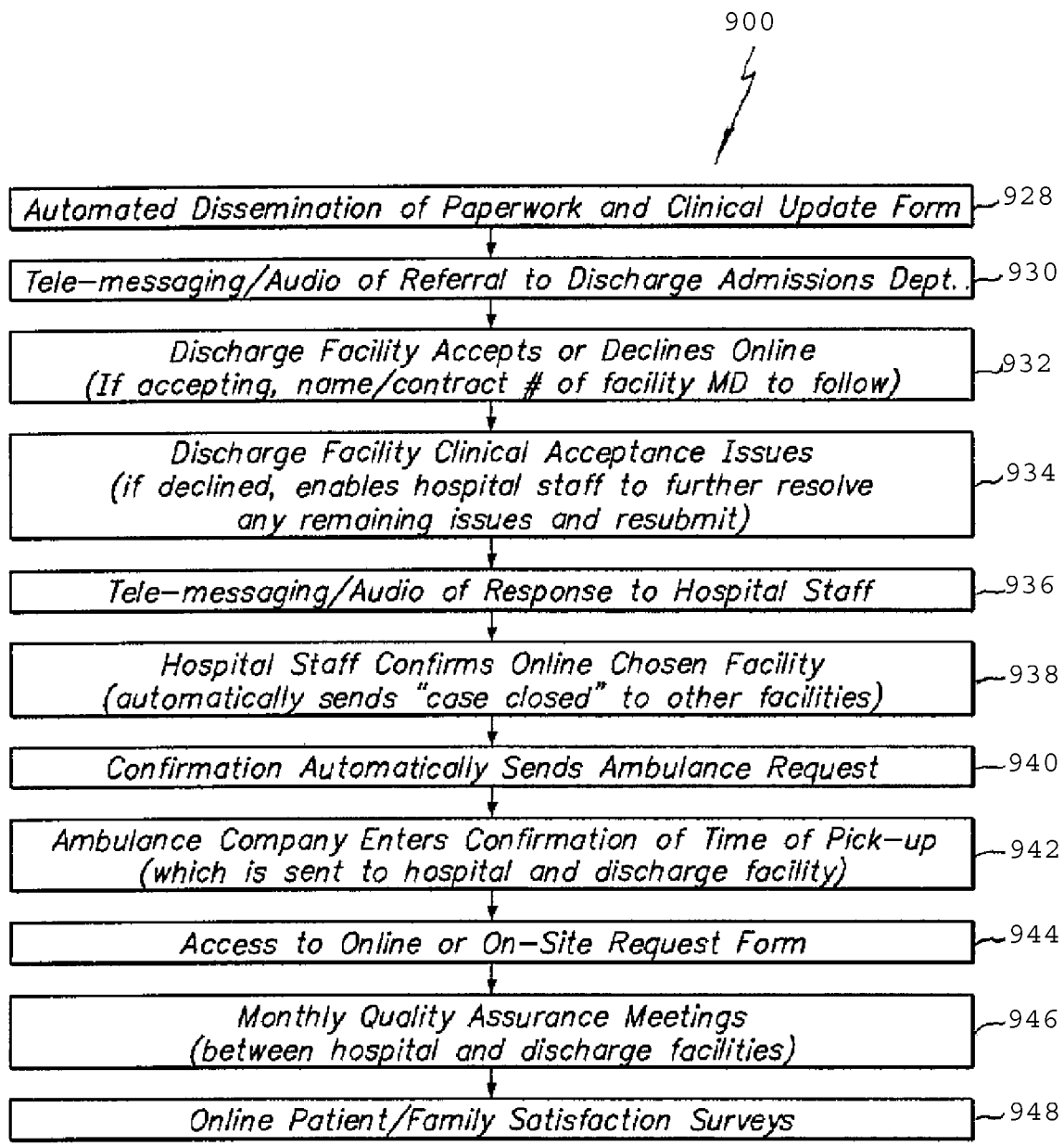

Continuing to FIG. 9B, the patient's medical paperwork and clinical update form are automatically disseminated typically via electronic facsimile transmission (e-fax) to each of the remote care facilities that the patient has been previously matched to as is illustrated in block 928. The information not transmitted can be available to the selected remote care facilities 104 from the system data storage memory across the network via of a password. Access to this patient information may be necessary in order for the remote care facilities to properly evaluate the patient's needs and to compare those needs to the capabilities and licensing restrictions of the remote care facility. The discharge department of the acute care hospital then enters into communications such as tele-messaging or audio communications with the Discharge Admissions Department of the remote care facility to which the discharged patient has been referred as is indicated in block 930. Thereafter, the discharge (remote care) facility after due diligence and evaluation of the record then either accepts or declines the admission of the patient as is indicated in block 932. This procedure typically occurs online and if accepting the patient, the remote care facility provides the name and contract number of the facility physician to the acute care hospital. However, if the remote care facility opts to decline the acceptance of the patient based upon clinical acceptance issues, the discharge department of the acute care hospital can resolve any remaining discharge issues and resubmit the patient referral as shown in block 934.

Once the remote care facility decides whether to accept or decline the patient referral, the remote care facility will send a corresponding tele-message or audio message to the discharge department of the acute care hospital 102 as a response to the patient referral as is illustrated in block 936. Thereafter, the discharge department of the acute care hospital sends an online confirmation of acceptance to the chosen remote care facility verifying the receipt of an acceptance decision as shown in block 193 in FIG. 9B. Simultaneously, the discharge department of the acute care hospital automatically sends a "case closed" message (typically online) to the remaining remote care facilities 104 matched to the patient. An additional feature is that the online confirmation from the discharge department of the acute care hospital to the chosen remote care facility automatically sends a request to a local ambulance company to transport the discharged patient from the acute care hospital to the chosen remote care facility on the discharge date as is shown in block 940. The local ambulance company then sends a confirmation of the scheduled time for pick-up of the patient and forwards this confirmatory message to both the acute care hospital and to the chosen remote care facility as shown in block 942. Thereafter, access to online or "on-site" request forms for case management in-services and conferences will be made available on the case management system website via the system web server as is shown in block 944. Furthermore, monthly quality assurance meetings between the acute care hospital and the chosen remote care facility will be conducted to track the progress of the discharged patient as is illustrated in block 946. Finally, online patient/family satisfaction surveys will be made available online to the patient and her family for expressing their level of satisfaction regarding the service provided by the case management system as is shown in block 948.

Figure 10:
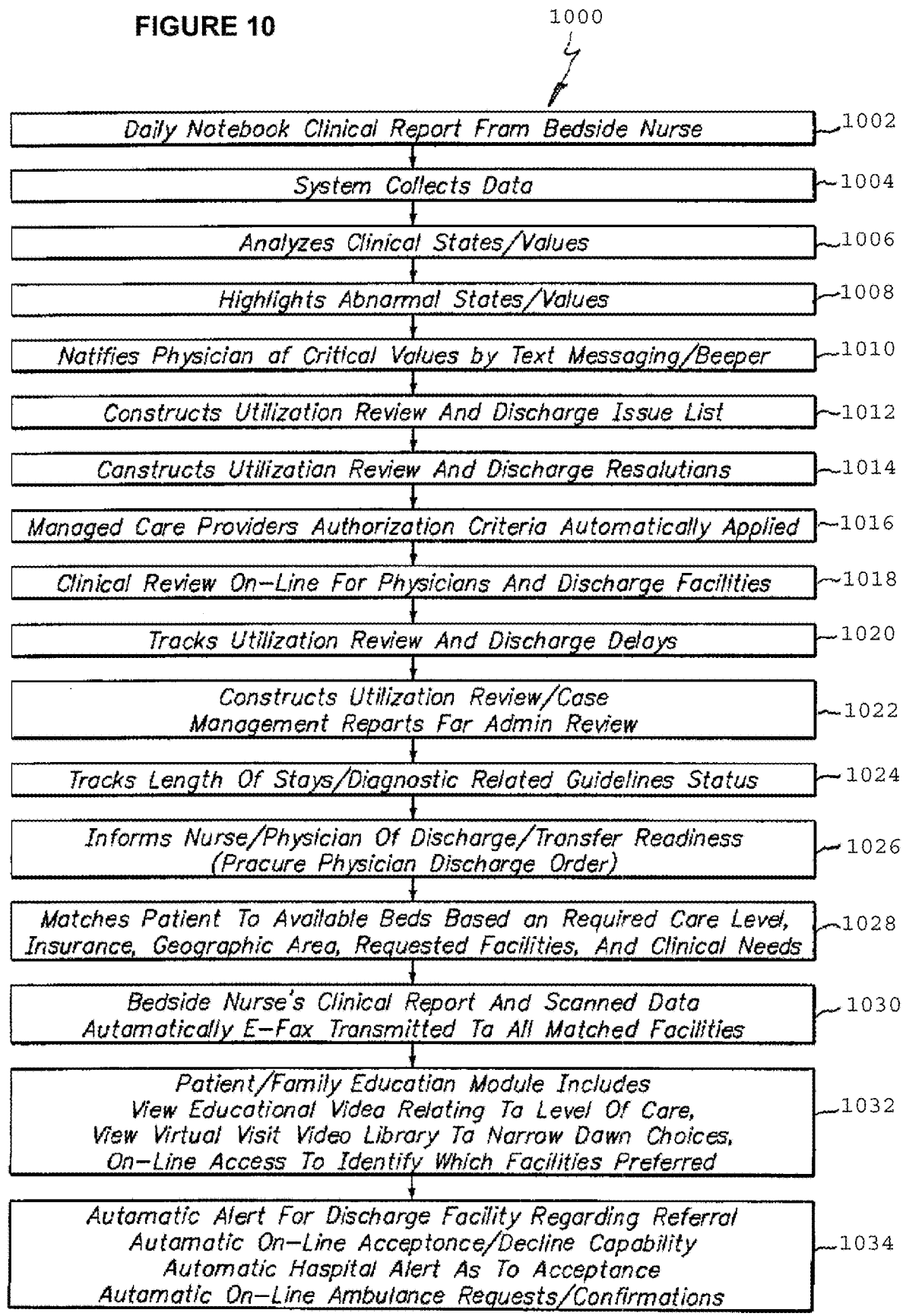
FIG. 10 illustrates another example discharge management process.

Reference is now made to FIG. 10 which is a flow diagram 1000 of the case management system 100 of FIG. 1 showing the process of preparing for the transfer of a patient from an acute care hospital environment to a discharge remote care facility. The process begins with a block 1002 which refers to the Daily Notebook Clinical Report which includes clinical data typically of multiple patients which can be manually entered daily into the data entry terminal by the bedside nurse. The clinical data recorded by the bedside nurse can then be collected by the case management system by being wirelessly transferred from the data entry terminal to the system server as is shown in block 1004. After the recorded clinical data can be transferred to the system server and stored in the system data storage memory, the computer program or software resident within the system server analyzes the patient's clinical states/values in block 1006 where clinical values include readings for body temperature, blood pressure, heart rate, respiration rate, and laboratory and culture results and the like. As a result of the analysis of the patient's clinical states/values, the abnormal clinical states/values are highlighted by the computer program to draw the attention of the hospital personnel as shown in block 1008. Such abnormal clinical states/values are important since they may raise discharge issues for the particular patient exhibiting the abnormal readings.

Because the abnormal clinical states/values exist, the hospital personnel will notify the physician of the abnormal readings by utilizing the Automated Physicians Assistant. This feature is typically employed after the patient's clinical states/values have been collected, wirelessly transferred to the system server and stored within the system data storage memory. The Automated Physicians Assistant transfers a message from the system server via the network to the mobile communication device carried by the physician as illustrated in block 1010 of FIG. 10. The message is typically transmitted to the mobile communications device via text messaging/beeper. Because of the abnormal clinical states/values provided by the particular patient, a utilization review and discharge issue list (not shown) recited in block 1012 is constructed which enumerates the patient discharge issues which could prevent the discharge of the patient according to schedule. Recall that one of the functions of the computer program of the system server is to formulate resolutions to the analyzed and identified patient discharge issues. Consequently, a utilization review and discharge resolutions to patient discharge issues can be constructed to assist hospital personnel in eliminating the discharge issues so that the patient can be discharged from the acute care hospital on schedule as is shown in block 1014. In the next block 1016, the authorization criteria or profile generated by the managed care provider or insurance company can be automatically applied to the patient's record as entered into the system data storage memory. This block 1016 makes the determination as to whether the insurance company will authorize payment for the patient's condition on a daily basis.

Once the patient's clinical data including any potential discharge issues is recorded in the system data storage memory, the physician and the selected remote care facilities can be notified online as indicated in block 1018 that the patient's case is available for clinical review online. The physicians who are treating the patient have access to the system data storage memory to review the patient's record as do other hospital personal via an assigned password. Likewise, once a patient discharge case is offered, the selected discharge remote care facility can also request a password for accessing the system data storage memory for reviewing the patient's clinical record. This procedure may be necessary to enable the selected remote care facility to determine if their facility is licensed and staffed to provide adequate care to the discharged patient. Thereafter, the case management system tracks the result of the utilization review and also discharge delays as indicated in block 1020. This block 1020 is necessary in order to provide the required information to constantly update the patient's projected discharge schedule. Next, the case management system constructs a utilization review/case management reports for review by the Administration Department of the acute care hospital as shown in block 1022. The Daily Case Management Report can be generated along with the Daily Nursing Report by the computer program resident within the system server and is employed for tracking the status of patient progress.

The next block 1024 in the process is that the case management system tracks the length of stays/diagnostic related guidelines status of each patient for record keeping purposes. This information which records the length of stay of a patient in the acute care hospital and compares it with the diagnostic related guidelines can be utilized to assist in determining the status of each patient. In the next block 1026, the case management system informs the nursing staff or physician of the discharge/transfer readiness, i.e., considering each of the steps in the procedure required to properly discharge the patient or to transfer the patient to one of the plurality of remote care facilities. If the discharge/transfer readiness is acceptable, the physician discharge order can be procured to complete the patient discharge/transfer authorization. Next, the patient can be matched to available beds according to current data collected from the remote care facilities. The patient bed matching can be based upon the patient required care level, insurance information provided by the managed care provider authorization criteria or profile, requested geographical area, requested facilities, and the clinical needs of the patient as is set forth in block 1028. Once the patient is matched to one or more beds available in the remote care facilities, the bedside nurse's clinical report and other patient medical data can be scanned and automatically transmitted via electronic facsimile (i.e., e-fax) as shown in block 1030 to all remote care facilities that were matched to the patient's case. In the next block 1032, the patient/family education module can be made available to the patient and her family for review. The education module includes (a) viewing an education video relating to the level of care required by the patient, (b) viewing a virtual visit video library to narrow down the choices of remote care facilities available to the patient and her family, and (c) having online access over the network for identifying which remote care facilities are preferred by the patient and her family.

The final block 1034 in FIG. 10 in the process practiced by the case management system is the automatic alert transmitted to the patient selected discharge remote care facility advising of the patient discharge referral. This automatic alert can be facilitated in several ways including an online transmission which audibly announces itself at the remote care facility. Clearly, the acute care hospital should receive a prompt response from the selected remote care facility to facilitate a timely scheduled patient discharge. Consequently, the selected remote care facility includes an automatic online acceptance or decline capability as to the patient discharge referral. The selected remote care facility after due diligence responds to the acute care hospital either accepting or declining the patient referral. In the case of a patient acceptance, the acute care hospital generates an automatic alert to confirm acceptance by the selected remote care facility and advises all other suitable remote care facilities of the match and acceptance by the selected remote care facility. Thereafter, an automatic online communication can be sent to a local ambulance company requesting service to transport the patient from the acute care hospital to the selected remote care facility on the appointed day. The ambulance company then responds with an automatic online confirmation as to the requested service. If the selected remote care facility declines the patient referral, the acute care hospital will offer the referral to the next remote care facility selected by the patient and her family.

Figure 11:
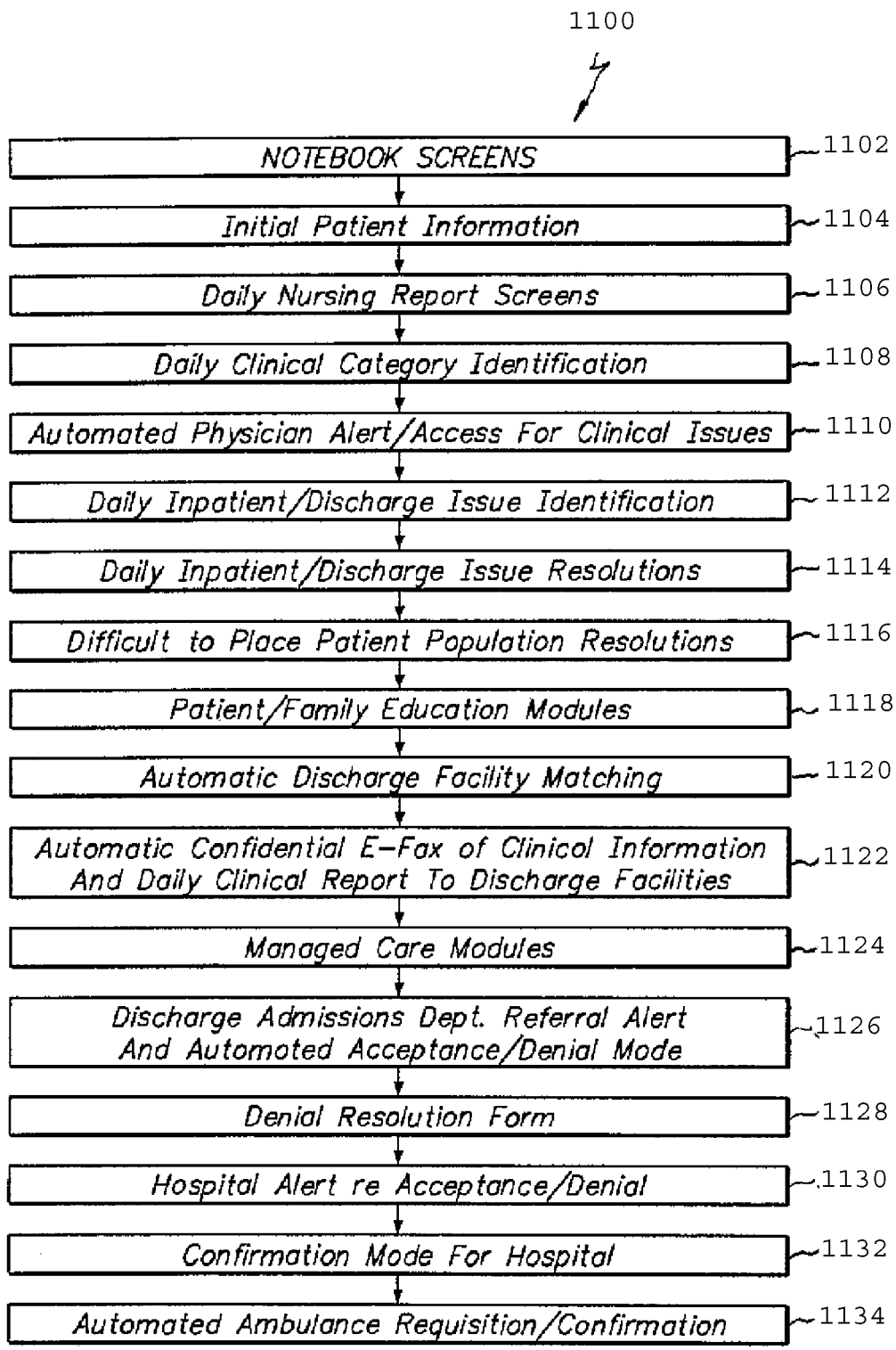
FIG. 11 illustrates another example discharge management process.

Reference is now made to FIG. 11 which is a flow diagram 1100 of the case management system 100 of FIG. 1 showing the process of transferring a patient from the acute care hospital environment to a discharge remote care facility. This process begins with the block 1102 of entering the personal information of the patient into the data entry terminals to create notebook screens that make this patient personal data readily available in the case management system. In the next block 1104, the patient personal data entered into the data entry terminals can be stored as the initial patient information which serves as the basis of the patient's hospital record. The clinical data entered by the bedside nurse used to create the Daily Nursing Report can be then utilized to create daily nursing report screens available for viewing over the network with a suitable password as is shown in block 1106. The case management system then creates the daily clinical category identification in block 1108 which identifies the categories of patients and their specific medical problems. With this information related to the clinical categories of the patients, the physician can be alerted by the automated physician's assistant for clinical data stored in the system data storage memory. In the alternative, the physician has access to the system server via an assigned password to investigate clinical issues, or can be contacted by hospital personnel regarding patient clinical issues via text messaging/beeper as recited in block 1110.

In an effort to anticipate clinical issues associated with patients and to minimize delays in their projected discharge dates, a daily patient/discharge issue identification list can be generated by the case management system as shown in block 1112 In FIG. 11. This list is compiled from the results of the analysis and identification functions of the computer program resident within the system server. Likewise, the next block 1114 describes a daily patient/discharge issue resolution list which can be generated by the results of the resolution function of the computer program resident within the system server. The resolution list may propose solutions to the patient discharge issues analyzed and identified by the computer program resident within the system server. In addition to the identification and resolution of patient discharge issues by the computer program, a certain population of patients can be identified as being difficult to place in any remote care facility as is noted in block 1116. These patients include those with severe medical problems. Algorithms for difficult placement populations are available on the case management system. Specific discharge pathways will offer solutions for bariatric, psychiatric, extensive wound, tuberculosis, and chemo/radiation patients. A list of durable medical supply companies who may offer resolutions to bariatric, wound vac, wound treatments, isolation equipment and alternative safety devices will be available for the hospital discharge team.

At the time of discharge, the patient and her family have access to the education modules as indicated in block 1118 in FIG. 11. The patient and family education modules and videos will be available for discharge support and to explain the discharge process and the services offered by the discharge remote care facilities, and to answer questions. The next block 1120 in the process is the automatic discharge facility matching, i.e., the matching of the patient to be discharged with the remote care facilities having the facilities, staff, capability and bed availability to provide the level of care required by the discharged patient. The bed availability and discharge facility matching program associated with the case management system enables the patient's sex, location desired, isolation type, insurance information and need for hemodialysis to be entered as data into the system server. Daily updates of the bed availabilities of the remote care facilities will be entered into the case management system. Profiles of the remote care facilities will be available setting forth the specific services rendered. In particular, copies of the profiles of the matched discharge remote care facilities are printed for patient records and distributed to patient family members. The information provided will include the name, location, contact information and services provided by each matched remote care facility. Once the data is entered, the case management system will display a list of matching facilities that meet the specific criteria for the patient's case. The case management system then assigns an identification code to the patient's case for communicating with the selected remote care facilities.

Thereafter, clinical information and daily clinical reports of the patient are automatically and confidentially transmitted via electronic facsimile (e-fax) to the matched discharge remote care facilities as illustrated in block 1122 on FIG. 11. Once a patient has been matched to a group of discharge remote care facilities, the discharge personnel of the acute care hospital will transmit typically online or via e-fax the patient's identifying information followed by specific medical information including history and physical, current medication list, the most recent notes by the physician, recent nursing notes, all culture and current chemistry/CBC results, physical therapy information, occupational and speech notes, latest chest x-ray result if available, and hemodialysis orders and notes if available. The patient's information will be sent to all matched and authorized discharge remote care facilities without the requirement of multiple transmissions. The case management system will be Health Insurance Portability and Accountability Act of 1996 (HIPAA) compliant. Furthermore, once the matched discharge remote care facilities have been identified, the patient and her family will be provided access to a virtual visit video library (not shown). This video library is comprised of video presentations of the matched discharge remote care facilities that may be viewed by the patient and/or her family members in order to assist them in the selection of their desired facility. These video presentations will contain images of the neighborhood in which the facility resides, the exterior and interior of the remote care facility, interviews with the Administrator, Director of Nursing, nurses, respiratory and/or physical therapists, and social work department members.

Once the patient's clinical information and daily clinical report have been e-fax transmitted to the matched discharge remote care facilities, the computer program investigates the managed care modules as illustrated in block 1124 of FIG. 11. In particular, managed care providers or insurance companies will provide insurance consultation and educational services to patients and their family members to assist them with their insurance claims and questions. Furthermore, social services support will also be provided to those patients requesting such services. Next, the discharge admissions department of the acute care hospital transmits a referral alert to the matched remote care facilities in an automated acceptance/denial mode as shown in block 1126. Once the patient's medical information has been sent to the designated discharge remote care facilities, each admissions officer of the matched remote care facilities will receive a distinctive referral alert which can be an online audio beep signal. This distinctive alert signal may alert the admissions officer that a referral has been received from the acute care hospital and the associated referral documents are available for viewing on the case management system with the use of an assigned password. The admissions officer of each remote care facility can be required to accept or deny the patient referral within a fixed response time.

The patient's medical paperwork as well as the updated standardized clinical form information will be accessible online over the network for use by the admission departments of the discharge remote care facilities. Access to the system data storage memory to access the patient's medical and clinical information can be made possible by assigning the remote care facilities receiving a patient referral a password. The availability of this information online makes it unnecessary for multiple evaluations of the patient by multiple remote care facilities. The acute care hospital will consent and take responsibility for the accuracy of the clinical state of the patient as set forth on the standardized clinical forms and documents available online for review by the remote care facilities. Specifically, if a patient is transferred to a remote care facility and the clinical state of the patient does not match the information set out on the standardized clinical form, the acute care hospital will be responsible for the transfer back to the acute care hospital and re-admission of the patient.

Once the admissions department of a discharge remote care facility has made a decision regarding the acceptance or declination of a patient, the decision will be entered into the case management system via the network. The discharge admissions department of the acute care hospital will receive a distinctive alert signal such as, for example, an online audio beep, advising them that a response is available on the case management system. The discharge remote care facility will be provided the option to complete a "Request Form" which will identify certain clinical or insurance issues that may have been a factor in the inappropriateness of the patient admission into the remote care facility. This "Request Form" or "Denial Resolution Form" is shown as block 1128 on FIG. 11 and is optional but encouraged as there are many clinical and/or insurance issues that can be resolved once the acute care hospital is aware of them. The referral of the refused patient may then be re-submitted to the discharge remote care facility for reconsideration. Thereafter, the discharge admissions department of the acute care hospital will transmit another distinctive referral alert which can once again be an online audio beep signal. This distinctive alert signal may alert the admissions officer at the remote care facility that a re-submission referral has been received from the acute care hospital as shown in block 1130. Further, the alert indicates that the re-submission referral documents are available for viewing on the case management system. The admissions officer of the remote care facility will then promptly respond with an acceptance or denial of the patient being reconsidered.

The discharge department personnel of the acute care hospital, the physician and/or patient and her family members then decide which of the accepting discharge remote care facilities they desire the patient to be admitted to. Then the discharge personnel of the acute care hospital will send a confirmation notice to the selected discharge remote care facility as indicated in block 1132. The admissions officer of the selected remote care facility will receive another distinctive online audio beep from the acute care hospital in confirmation mode to advise the admissions officer that their remote care facility has been chosen to receive the patient. This step in the process is known as the confirmation mode for hospital. The admissions officer of the chosen remote care facility will then enter their formal confirmation of acceptance of the patient in the case management system along with the name and phone number of their assigned admitting physician. Thereafter, the discharge department of the acute care hospital will (1) receive a distinctive online audio beep indicating that the chosen remote care facility 104 has confirmed acceptance, and (2) verify that the name and telephone number of the admitting physician assigned to the chosen remote care facility has been entered into the case management system.

Thereafter, the case management system will automatically request ambulance assistance which can be done in an online mode specifying a date and time. The local ambulance company will then confirm the request for services verifying the date and time in a responsive online message. Then, the discharge department of the acute care hospital will enter the date and time that the ambulance from the local ambulance company will arrive to transport the patient to the chosen remote care facility. This action by the discharge department of the acute care hospital will then initiate yet another distinctive online audio beep directed from the acute care hospital to the admissions officer of the chosen remote care facility verifying the confirmation of scheduled services by the ambulance company. The admissions officer of the chosen remote care facility will have password access to the time of arrival information located in the system server via the network so that the chosen remote care facility can be prepared to receive the discharged patient.

Regarding another feature, the case management system includes "continuous isolation status monitoring" which enables the computer program resident within the system server to keep track of current culture results as specific to designated discharge level. For example, certain remote care facilities such as, for example, a sub-acute facility will not isolate a patient with a history of certain infections if there are three consecutive negative culture results. However, an acute care hospital always isolates any patient with a history of the same infection regardless of subsequent negative culture results. The laboratory personnel of the acute care hospital will enter the results in the case management system and the computer program of the system server will update the current status of the patient as it relates to the culture results. This procedure enables the discharge department of the acute care hospital to be aware that they may obtain further cultures to rule out certain isolations if beds reserved for such isolations are not available at the discharge remote care facilities.

Another feature includes financial options that are made available to the discharge department of the acute care hospital for use with certain difficult-to-place patients such as, for example, straight Medi-Cal hemodialysis patients, Medi-Cal pending patients, and patients without health insurance. Additionally, request forms for case management in-services and conferences may be available on the website through the system web server. Continuing education credits for hospital and medical personnel are also available online on the system website. Further, on-site evaluations regarding case management services may be requested for certain cases with special circumstances. Guidelines under the Health Insurance Portability and Accountability Act of 1996 (Public Law 104-191) enacted by the 104th Congress and referred to as HIPAA can be posted on the website of the case management system. All HIPAA regulations will be enforced according to the spirit of the law. All subscribing facilities and their employees can be assigned passwords and educated regarding HIPAA compliance.

The case management system will track patient discharge data including length of hospitalization and time evolved from initial discharge consideration to the actual discharge date. It is anticipated that this tracking data will identify accumulated problems/issues that may have contributed to delays in the patient discharge process. Additionally, the case management system will provide a forum for assessing and communicating any discharge facility issues so that the relationship between the acute care hospitals and the discharge remote care facilities will be ongoing, supportive and resolution oriented. Scheduled meeting between the acute care hospitals and the discharge remote care facilities are encouraged and may be scheduled through the case management system. Problem solving conferences will be routinely posted on the case management system for the attendance of personnel from the acute care hospital and the discharge remote care facilities.

The case management system serves to integrate the needs relating to interactive communications, information, identification of discharge problems and resolutions therefore between the acute care hospital environment and hospital personnel, physicians, discharge remote care facilities, managed care providers such as insurance company (payers), patients and their families, and ancillary service providers such as ambulance companies, and home health care. In one embodiment, the case management system and method for use in an acute care hospital environment for placement of a patient upon discharge from the acute care hospital environment to a remote care facility comprises a plurality of portable data entry terminals for entering data for monitoring medical parameters of a patient in the hospital environment. A remotely located system server can be wirelessly connected to the portable data entry terminals for receiving, storing and providing access to the entered data, the system server including a computer program for analyzing the entered data, identifying and formulating resolutions to patient and discharge placement problems, and determining if and at what level the patient will be discharged. A system data storage memory can be housed within the system server for depositing and retrieving the entered data. A network can be in cyber communication with the system server and a plurality of remote care facilities in a secure online interactive mode for enabling access to the data stored in the system data storage memory from the portable data entry terminals 106 and the remote care facilities. Likewise, the network enables cyber communications between the remote care facilities and the portable data entry terminals in a secure online interactive mode for placement of the patient in one of the remote care facilities upon discharge of the patient from the hospital environment.

Certain embodiments provide novel advantages over other case management systems and/or methods for use in acute care hospital environments including (1) facilitating the transfer of patients from the acute care hospital to a remote care facility 104 such as sub-acute medical and other skilled nursing facilities upon the discharge of the patient from the acute care hospital, (2) utilizing a secure online interactive case management system which can be accessible to all password authorized users, (3) providing a case management system that performs the function of and eliminates the need for hospital employed and managed care provider/insurance company employed case managers, (4) facilitating the daily bedside collection of patient clinical data by bedside nurses for direct entry into the system data storage memory for subsequent authorized access, (5) assisting the physician in tracking the healing progress of patients, (6) providing a more streamlined efficient process for intelligent matching of a scheduled discharge patient with a suitable remote care facility, (7) providing the patient and her family with online access for virtual touring and inspecting of remote care facilities, (8) identifying and alerting hospital personnel to patient discharge issues and creating resolutions to those discharge issues, (9) providing improved communications between the nursing staff, hospital discharge personnel, physicians and the patient's family members, and (10) providing a more cost effective process for managed care providers or insurance companies by moving patients out of the acute care hospital and into a remote care facility on schedule.

CONCLUSION

In general, the word "module," as used herein, is used in its broad and ordinary sense and refers, for example, to logic embodied in hardware or firmware, or to a collection of software instructions, possibly having entry and exit points, written in a programming language, such as, for example, Java, C, or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays, application-specific circuits, or hardware processors. The modules described herein are preferably implemented as software modules, but may be represented in hardware or firmware. Generally, the modules described herein refer to logical modules that may be combined with other modules or divided into sub-modules despite their physical organization or storage.

The various illustrative logical blocks, modules, data structures, algorithms, equations, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, data structures, and processes described herein may be implemented or performed by a machine, such as a computer, a processor, a digital signal processor (DSP), an application specific integrated circuit (ASIC), a filed programmable gate array (FPGA) or other programmable logic device, discrete gate or transistor logic, discrete hardware components, or any combination thereof designed to perform the functions described herein. A processor may be a microprocessor, a controller, a microcontroller, a state machine, combinations of the same, or the like. A processor may also be implemented as a combination of computing devices—for example, a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware or firmware, in a software module executed by a hardware processor, or in a combination of the two. For example, each of the processes described above may also be embodied in, and fully automated by, software modules executed by one or more machines such as computers or computer processors. A module may reside in a non-transitory computer-readable storage medium such as RAM memory, flash memory, ROM memory, EPROM memory, EEPROM memory, registers, a hard disk, a removable disk, a CD-ROM, a DVD, memory capable of storing firmware, or any other form of computer-readable storage medium. An exemplary computer-readable storage medium can be coupled to a processor such that the processor can read information from, and write information to, the computer readable storage medium. In the alternative, the computer-readable storage medium may be integral to the processor. The processor and the computer-readable storage medium may reside in an ASIC. Hardware components may communicate with other components via wired or wireless communication networks such as, e.g., the Internet, a wide area network, a local area network, or some other type of network.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). For example, features described with respect to the repatriation management system may be applied to and incorporated into the discharge management system. Similarly, features described with respect to the discharge management system may be applied to and incorporated into the repatriation management system. Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The following is claimed:

1. A non-transitory computer storage medium having stored thereon program instructions for repatriating a patient from an out of network admitting hospital to an in network destination hospital configured to be executed by a processor, wherein the instructions when executed by the processor are configured to:
   access from a computer storage medium patient data, including at least qualifying criteria for admission to a hospital comprising a list of ambulance providers associated with an insurer of the patient;
   access from a computer storage medium candidate destination hospital data including at least admission criteria associated with a plurality of candidate destination hospitals;
   automatically match the patient to one or more of the candidate destination hospitals based at least upon the qualifying criteria and the admission criteria;
   automatically generate a list of candidate destination hospitals automatically matched to the patient; generate data configured to display a graphical user interface configured to: display one or more repatriation requests along with corresponding one or more repatriation selectors;
   receive, via the graphical user interface, user selection of a repatriation selector corresponding with a displayed repatriation request associated with the patient;
   display, in response to the user selection of the repatriation selector and based on the list of candidate destination hospitals, the list of candidate destination hospitals matched to the patient;
   receive, via the graphical user interface, user selection of a candidate destination hospital;
   electronically transmit, based on the user selection of the candidate destination hospital and on the qualifying criteria associated with the candidate destination hospital, the request to the selected candidate destination hospital;
   display, in response to transmitting the request to the selected destination hospital, a cancel selector selectable by a user, the cancel selector configured to allow a user to cancel the request before the request is accepted by the selected candidate destination hospital;
   electronically receive an acceptance of the repatriation request from the selected destination hospital;
   display, in response to receiving the acceptance of the repatriation request from the selected destination hospital and based at least in part on the list of ambulance providers, an ambulance-request selector selectable by a user, the ambulance-request selector configured to indicate at least that the acceptance of the repatriation request from the selected destination hospital;
   receive, via the graphical user interface, user selection of the ambulance-request selector;
   transmit to at least one ambulance provider, based at least on the selection of the ambulance-request selector and on the list of ambulance providers, an ambulance request configured to schedule transport of the patient to the selected candidate destination hospital;
   receive, from one of the at least one ambulance providers, acceptance of the ambulance request; and
   display, in response to receiving the acceptance of the ambulance request from the ambulance provider, an indication of acceptance of the ambulance request.

2. The non-transitory computer storage medium of claim 1, wherein the program instructions, when executed by the processor, are further configured to:
   receive a patient-specific code; and
   in response to receiving the patient-specific code, automatically access the patient data.

3. The non-transitory computer storage medium of claim 2, wherein the patient-specific code is received from a QR scanner or barcode scanner.

4. The non-transitory computer storage medium of claim 3, wherein:
   the patient-specific code indicates admission to an admitting hospital, and
   the graphical user interface is further configured to automatically transmit an alert to an insurance agency associated with the patient upon receiving the patient-specific code indicating admission to the admitting hospital.

5. The non-transitory computer storage medium of claim 1, wherein:
   the patient data further includes one or more medical parameters of the patient,
   the candidate destination hospital data includes one or more clinical capabilities of the candidate destination hospitals, and
   the automatically matching the patient to one or more of the candidate destination hospitals is further based at least upon matching the medical parameters of the patient and the clinical capabilities of the candidate destination hospitals.

6. The non-transitory computer storage medium of claim 1, wherein the program instructions, when executed by the processor, are further configured to:
   electronically receive, from three or more of the at least one ambulance provider, acceptance of the ambulance request, and display, via the graphical user interface, the acceptances of the ambulance request to the admitting hospital, and
   electronically receive, via the graphical user interface, a selection from among the accepting ambulance providers.

7. The non-transitory computer storage medium of claim 6, wherein the program instructions, when executed by the processor, are further configured to electronically notify an insurer of the patient of the selected ambulance provider.

8. A method for managing requests for repatriating a patient from an out-of-network admitting hospital to an in-network destination hospital, the method comprising:
   automatically matching the patient to one or more candidate destination hospitals, wherein the automatically matching comprises:
      accessing from a computer storage medium patient data including at least insurance network information for the patient comprising a list of ambulance providers associated with the patient's insurer;
      accessing from a computer storage medium data regarding candidate destination hospitals, the data including at least insurance network information for the candidate destination hospitals; and automatically matching the insurance network information of the patient and the insurance network information of the candidate destination hospitals;

generate data configured to display a graphical user interface configured to:

display one or more repatriation requests along with corresponding one or more repatriation selectors;

receive user selection of a repatriation selector corresponding with a displayed repatriation request associated with the patient;

display, in response to the user selection of the repatriation selector and based on the candidate destination hospitals, the candidate destination hospitals matched to the patient;

receive, via the graphical user interface, user selection of a candidate destination hospital;

electronically transmit, based on the user selection of the candidate destination hospital and on the qualifying criteria associated with the candidate destination hospital, the request to the selected candidate destination hospital;

display, in response to transmitting the request to the selected destination hospital, a cancel selector selectable by a user, the cancel selector configured to allow a user to cancel the request before the request is accepted by the selected candidate destination hospital;

electronically receive an acceptance of the repatriation request from the selected destination hospital;

display, in response to receiving the acceptance of the repatriation request from the selected destination hospital and based at least in part on the list of ambulance providers, an ambulance-request selector selectable by a user, the ambulance-request selector configured to indicate at least that the acceptance of the repatriation request from the selected destination hospital; receive, via the graphical user interface, user selection of the ambulance-request selector;

transmit to at least one ambulance provider, based at least on the selection of the ambulance-request selector and on the list of ambulance providers, an ambulance request configured to schedule transport of the patient to the selected candidate destination hospital;

receive, from one of the at least one ambulance providers, acceptance of the ambulance request; and display, in response to receiving the acceptance of the ambulance request from the ambulance provider, an indication of acceptance of the ambulance request.

9. The method of claim 8, further comprising receiving a patient-specific code from a QR or barcode scanner, and in response to receiving the patient-specific code, automatically accessing the patient data.

10. The method of claim 9, wherein the patient-specific code indicates admission to the admitting hospital, the method further comprising automatically alerting an insurer of the patient upon receiving the patient-specific code indicating admission to the admitting hospital.

11. The method of claim 8, wherein:
the patient data further includes one or more medical parameters of the patient,
the data regarding candidate destination hospitals includes one or more clinical capabilities of the candidate destination hospitals, and
the automatically matching the patient to one or more of the candidate destination hospitals is further based at least upon matching the medical parameters of the patient and the clinical capabilities of the candidate destination hospitals.

12. The method of claim 8, further comprising:
electronically receiving, from three or more of the ambulance providers, acceptance of the ambulance request, and electronically transmitting the acceptances of the ambulance request to the graphical user interface;

electronically receiving, via the graphical user interface, a selection from among the accepting ambulance providers; and electronically transmitting, based on the selection from among the accepting ambulance providers, a notification to an insurer of the patient of the selected ambulance provider.

13. A system for repatriating a patient from an out-of-network admitting hospital to an in-network destination hospital, said system comprising:
one or more hardware processors;
physical computer storage configured to store:
patient data including at least insurance network information for the patient;
candidate destination hospital data including at least insurance network information for candidate destination hospitals; and
instructions that, when executed by one or more hardware processors, are configured to:
access patient data including at least qualifying criteria for admission to a hospital comprising a list of ambulance providers associated with an insurer of the patient;
access candidate destination hospital data including at least admission criteria associated with a plurality of candidate destination hospitals;
automatically match the patient to one or more of the candidate destination hospitals based at least upon the qualifying criteria and the admission criteria;
automatically generate a list of candidate destination hospitals automatically matched to the patient;
generate data configured to display a graphical user interface configured to:
display one or more repatriation requests along with corresponding one or more repatriation selectors;
receive, via the graphical user interface, user selection of a repatriation selector corresponding with a displayed repatriation request associated with the patient;
display, in response to the user selection of the repatriation selector and based on the list of candidate destination hospitals, the list of candidate destination hospitals matched to the patient;
receive, via the graphical user interface, user selection of a candidate destination hospital;
electronically transmit, based on the user selection of the candidate destination hospital and on the qualifying criteria associated with the candidate destination hospital, the request to the selected candidate destination hospital;
display, in response to transmitting the request to the selected destination hospital, a cancel selector selectable by a user, the cancel selector configured to allow a user to cancel the request before the request is accepted by the selected candidate destination hospital;

electronically receive an acceptance of the repatriation request from the selected destination hospital;

display, in response to receiving the acceptance of the repatriation request from the selected destination hospital and based at least in part on the list of ambulance providers, an ambulance-request selector selectable by a user, the ambulance-request selector configured to indicate at least that the acceptance of the repatriation request from the selected destination hospital;

receive, via the graphical user interface, user selection of the ambulance-request selector;

transmit to at least one ambulance provider, based at least on the selection of the ambulance-request selector and on the list of ambulance providers, an ambulance request configured to schedule transport of the patient to the selected candidate destination hospital;

receive, from one of the at least one ambulance providers, acceptance of the ambulance request; and display, in response to receiving the acceptance of the ambulance request from the ambulance provider, an indication of acceptance of the ambulance request.

14. The system of claim 13, wherein the instructions, when executed by one or more hardware processors, are further configured to display an indication that a patient-specific code may be entered by scanning a QR code or barcode to automatically obtain patient data.

15. The system of claim 13, wherein the instructions, when executed by one or more hardware processors, are further configured to:

indicate, via the graphical user interface, acceptances of the transport request from three or more of the at least one medical transport providers; and receive, via the graphical user interface, a selection of one of the accepting medical transport providers.

16. The system of claim 15, wherein the instructions, when executed by one or more hardware processors, are configured to receive a request, via the graphical user interface, to alert an insurer of the patient of the selection of the accepting medical transport provider.

17. The system of claim 13, wherein the instructions, when executed by one or more hardware processors, are further configured to indicate, via the graphical user interface, that the transport request from the admitting hospital has been cancelled.

* * * * *